United States Patent
Spear et al.

(10) Patent No.: US 10,793,864 B2
(45) Date of Patent: Oct. 6, 2020

(54) METHODS AND COMPOSITIONS FOR ASSESSING VIRAL NUCLEAR LOCALIZATION

(71) Applicant: GEORGE MASON UNIVERSITY, Fairfax, VA (US)

(72) Inventors: Mark Spear, Fairfax, VA (US); Yuntao Wu, Fairfax, VA (US)

(73) Assignee: GEORGE MASON UNIVERSITY, Fairfax, VA (US)

( * ) Notice: Subject to any disclaimer, the term of this patent is extended or adjusted under 35 U.S.C. 154(b) by 462 days.

(21) Appl. No.: 15/389,834

(22) Filed: Dec. 23, 2016

(65) Prior Publication Data

US 2017/0191068 A1     Jul. 6, 2017

Related U.S. Application Data

(60) Provisional application No. 62/274,049, filed on Dec. 31, 2015.

(51) Int. Cl.
| | |
|---|---|
| *C12N 15/62* | (2006.01) |
| *C07K 14/005* | (2006.01) |
| *C12N 7/00* | (2006.01) |
| *C12Q 1/02* | (2006.01) |
| *C12Q 1/66* | (2006.01) |
| *C07K 14/47* | (2006.01) |
| *C07K 14/435* | (2006.01) |
| *C09K 11/06* | (2006.01) |

(52) U.S. Cl.
CPC ........ *C12N 15/62* (2013.01); *C07K 14/43595* (2013.01); *C07K 14/4702* (2013.01); *C09K 11/06* (2013.01); *C12N 7/00* (2013.01); *C12Q 1/02* (2013.01); *C12Q 1/66* (2013.01); *C07K 2319/61* (2013.01); *C09K 2211/1088* (2013.01); *C09K 2211/1441* (2013.01); *C12N 2740/15023* (2013.01); *C12N 2740/16023* (2013.01)

(58) Field of Classification Search
None
See application file for complete search history.

(56) References Cited

PUBLICATIONS

McDonald et al. "Visualization of the intracellular behavior of HIV in living cells", J. Cell Biol. 2002; 159(3): 441-452.*
Butler SL, et al., "A quantitative assay for HIV DNA integration in vivo", Nat. Med. (2001); 7(5):631-4.
Cameron PU, et al., "Establishment of HIV-1 latency in resting CD4+ T cells depends on chemokine-induced changes in the actin cytoskeleton", Proc Natl Acad Sci USA (2010); 107(39):16934-9.
Campbell EM, et al., "Labeling HIV-1 virions with two fluorescent proteins allows identification of virions that have productively entered the target cell", Virology. (2007); 360(2):286-93.
Cavrois M, et al., "A sensitive and specific enzymebased assay detecting HIV-1 virion fusion in primary T lymphocytes", Nat Biotechnol. (2002); 20(11): 1151-4.
Curtis DJ, et al., "The Molecular Basis of Lmo2-Induced T-Cell Acute Lymphoblastic Leukemia", Clin. Cancer Res. (2010); 16(23):5618-23.
Deane JE, et al., "Structural basis for the recognition of Idb1 by the N-terminal LIM domains of LMO2 and LMO4", Embo. J. (2003); 22(9):2224-2233.
Engelman A, et al., "Multiple effects of mutations in human immunodeficiency virus type 1 integrase on viral replication", J. Virol. (1995); 69(5):2729-36.
Gerlach LO, et al., "Molecular interactions of cyclam and bicyclam non-peptide antagonists with the CXCR4 chemokine receptor", J. Biol. Chem. (2001); 276(17):14153-60.
Guo J, et al., "Spinoculation Triggers Dynamic Actin and Cofilin Activity That Facilitates HIV-1 Infection of Transformed and Resting CD4 T Cells", J. Virol. (2011); 85(19):9824-9833.
Hall MP, et al., "Engineered luciferase reporter from a deep sea shrimp utilizing a novel imidazopyrazinone substrate", ACS Chem. Biol. (2012); 7(11):1848-57.
Kilzer JM, et al., "Roles of host cell factors in circularization of retroviral dna", Virology. (2003); 314(1):460-7.
Li C, et al., "FastCloning: a highly simplified, purification-free, sequence- and ligation-independent PCR cloning method" BMC Biotechnol. (2011); 11:92. PMCID: 3207894.
McDonald D, et al. "Visualization of the intracellular behavior of HIV in living cells", J. Cell. Biol. (2002) ;159(3):441-52.
Ryan DP, et al., "Assembly of the oncogenic DNA-binding complex LMO2-Ldb1-TAL1-E12", Proteins. (2008); 70(4):1461-74.
Unutmaz D, et al., "Cytokine Signals Are Sufficient for HIV-1 Infection of Resting Human T Lymphocytes", J. Exp. Med. (1999); 189(11):1735-46.
Wang W, et al., "A dichotomy in cortical actin and chemotactic actin activity between human memory and naive T cells contributes to their differential susceptibility to HIV-1 infection" J. Biol. Chem. (2012); 287(42):35455-35469.
Yoder A, et al., "HIV envelope-CXCR4 signaling activates cortical to overcome cortical actin restriction in resting CD4 T cells", Cell. (2008); 134(5): 782-92.

* cited by examiner

*Primary Examiner* — Stacy B Chen

(74) *Attorney, Agent, or Firm* — Dave Law Group LLC; Raj S. Dave

(57) ABSTRACT

In one aspect, the invention relates to methods and compositions for determining migration of a virus particle to the nucleus of a cell. This abstract is intended as a scanning tool for purposes of searching in the particular art and is not intended to be limiting of the present invention.

24 Claims, 17 Drawing Sheets
Specification includes a Sequence Listing.

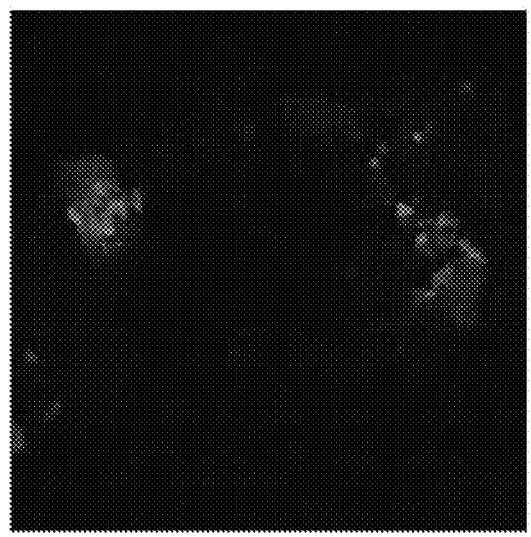
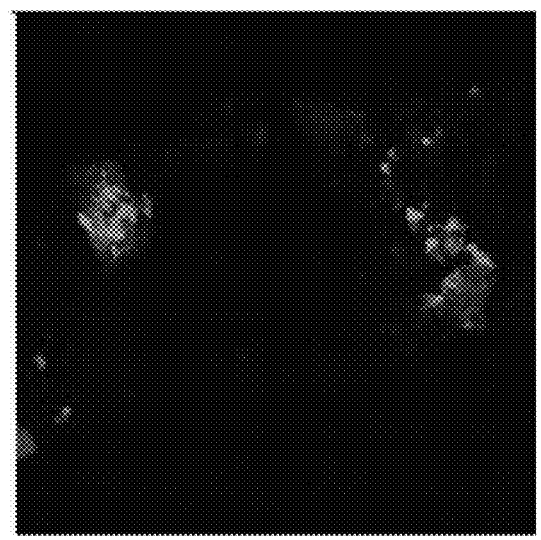
FIG. 2A  FIG. 2B
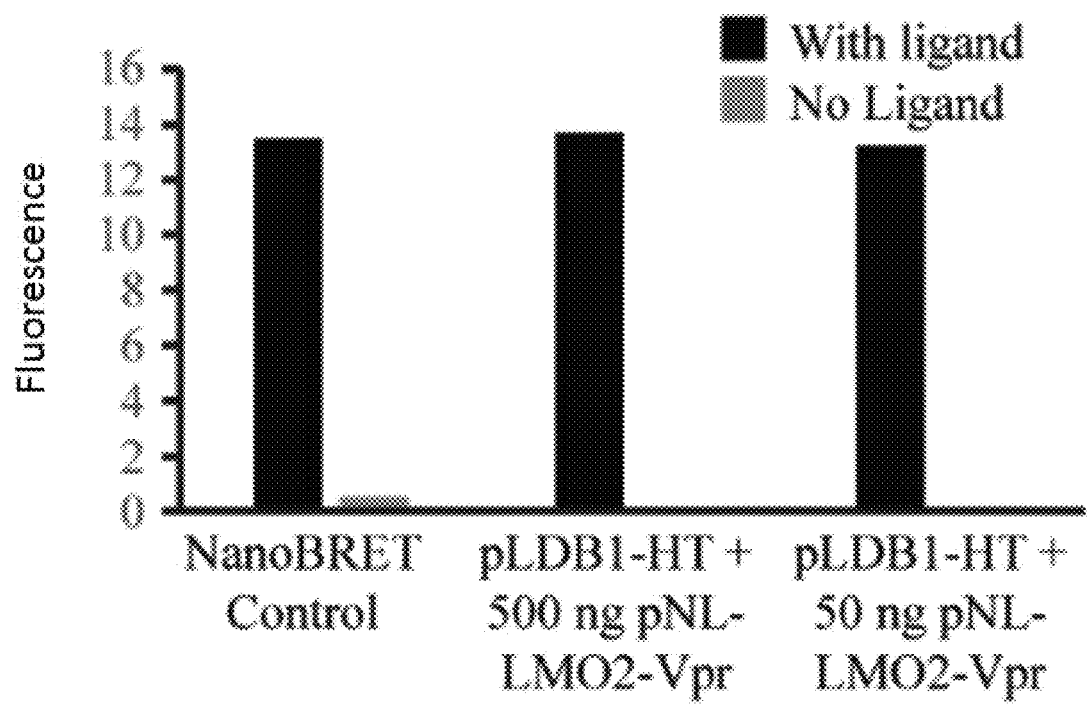
FIG. 2C

METHODS AND COMPOSITIONS FOR ASSESSING VIRAL NUCLEAR LOCALIZATION

CROSS-REFERENCE TO RELATED PATENT APPLICATIONS

This application claims the benefit of the filing date of U.S. Provisional Application No. 62/274,049, which was filed on Dec. 31, 2015. The content of this earlier filed application is hereby incorporated by reference herein in its entirety.

SEQUENCE LISTING

The Sequence Listing submitted herewith as a text file named "37552_0008U2_Sequence_Listing," created on Dec. 23, 2016, and having a size of 7,577 bytes is hereby incorporated by reference pursuant to 37 C.F.R. § 1.52(e)(5).

STATEMENT REGARDING FEDERALLY SPONSORED RESEARCH

This invention was made with government support under grant number AI110174 awarded by the National Institutes of Health. The government has certain rights in the invention.

BACKGROUND

Nuclear migration, e.g., HIV nuclear migration and integration, is a decisive step in the establishment of viral infection, or viral latency when cellular conditions are not favorable. Studying HIV nuclear migration is critically important for understanding regulations of viral infection and latency, as exemplified by recent studies showing dramatic effects on viral nuclear migration by chemokines. However, currently, no convenient tools for measuring HIV nuclear migration exist. At present, viral nuclear localization can be measured by a surrogate maker, the 2-LTR circle, which only accumulates in the nucleus. Viral nuclear DNA can also be directly measured by performing nuclear fractionation to quantify total viral DNA in the nucleus. Both of these assays have limitations. The 2-LTR circle quantification is insensitive at early time points (before 12 hours), and particularly in resting CD4 T cells, where 2-LTR circles are difficult to detect without T cell activation. Frequently, early nuclear migration in resting T cells can only be measured by nuclear fractionation, which requires multiple fractionation controls, and is both time-consuming and prone to experimental errors.

Despite advances in methods to determine nuclear migration, e.g., HIV nuclear migration and integration, there is still a scarcity of rapid, convenient, and sensitive methods and compositions to determine nuclear migration. These needs and other needs are satisfied by the present invention.

SUMMARY

In accordance with the purpose(s) of the invention, as embodied and broadly described herein, the invention, relates to compositions (e.g., recombinant DNA constructs) and methods for nuclear localization of a peptide, and kits comprising the recombinant DNA constructs described herein.

Disclosed are recombinant DNA constructs that comprise a promoter operably linked to a nucleotide sequence encoding a fusion protein comprising an LMO2 polypeptide, a reporter polypeptide, and a nuclear localization polypeptide.

Also disclosed are recombinant virus particles that comprise a fusion protein comprising an LMO2 polypeptide, a reporter polypeptide, and a nuclear localization polypeptide.

Also disclosed are methods of preparing the recombinant virus particles.

Also disclosed are recombinant DNA constructs that comprise a promotor operably linked to a nucleotide sequence encoding a fusion protein comprising an LDB1 polypeptide and a reporter polypeptide.

Also disclosed are recombinant cell lines comprising a recombinant DNA construct that comprise a promotor operably linked to a nucleotide sequence encoding a fusion protein comprising an LDB1 polypeptide and a reporter polypeptide.

Also disclosed are kits comprising one or more of a disclosed recombinant DNA construct comprising a promotor operably linked to a nucleotide sequence encoding a fusion protein comprising an LMO2 polypeptide, a reporter polypeptide, and a nuclear localization polypeptide; a disclosed recombinant virus particle that comprise a fusion protein comprising an LMO2 polypeptide, a reporter polypeptide, and a nuclear localization polypeptide; a disclosed recombinant DNA construct that comprises a promotor operably linked to a nucleotide sequence encoding a fusion protein comprising an LDB1 polypeptide and a reporter polypeptide; a recombinant cell line that comprises a recombinant DNA construct that comprise a promotor operably linked to a nucleotide sequence encoding a fusion protein comprising an LDB1 polypeptide and a reporter polypeptide; and the use of one of the foregoing in a method to determine nuclear localization.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

FIGS. 2A-2D show representative data showing that LDB1 and LMO2 interact in the context of the disclosed fusion proteins. Briefly, FRET is observed when the fusion construct, EGFP-LMO2-Vpr, and the fusion construct, LDB1-mCherry, are cotransfected into HEK293T cells (see FIGS. 2A and 2B). Bioluminescence resonance energy transfer ("BRET") was observed in a BRET control, as well as when the fusion constructs, NL-LMO2-Vpr and Ldb1-HaloTag, are cotransfected, but only when HaloTag ligand is provided (see FIG. 2C). BRET is also observed when the fusion construct, NL-LMO2-Vpr, is virally transduced into HEK293T cells transfected with a recombinant DNA construct encoding a Ldb1-HaloTag fusion protein (see FIG. 2D). BRET is only observed when HaloTag ligand in provided.

FIG. 9A shows vLKO.1 MCS Puro Ldb1-HT polyclonal transduced cells (FACS R110 direct ligand). FIG. 9B shows vLKO.1 MCS Puro Ldb1-HT transduced HeLa JC53 representative clones (FACS R110 direct ligand). FIG. 9C shows vLKO.1 MCS Puro Ldb1-HT transduced A3R5.7 representative clones (FACS R110 direct ligand).

FIG. 10A is a bar graph showing the summary of vLKO.1 MCS Puro Ldb1-HT transduced HeLa JC53 clones tested (FACS R110 direct ligand). FIG. 10B is a bar graph showing the summary of vLKO.1 MCS Puro Ldb1-HT transduced A3R5.7 clones tested (FACS R110 direct ligand).

Figure 1A:
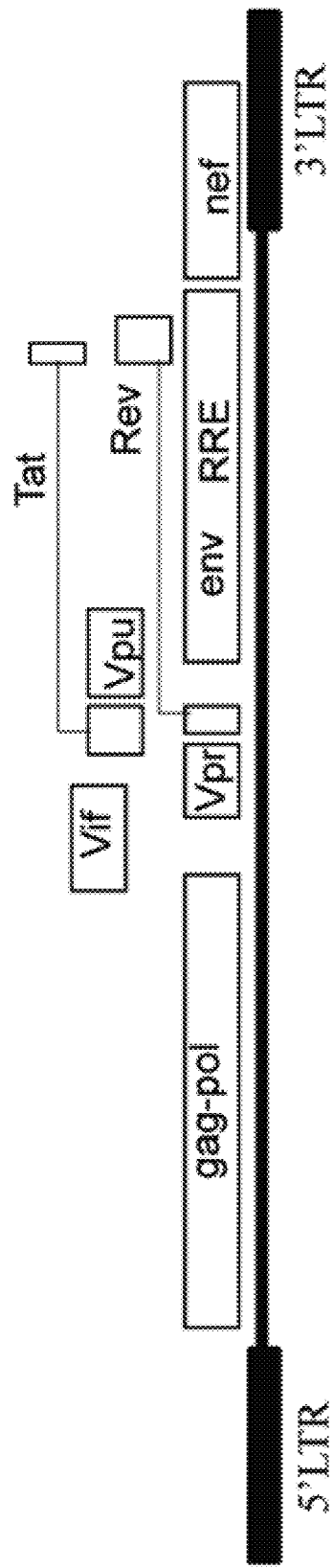
FIG. 1A shows a schematic representation of pNL4-3 (alternatively referred to as the HIV-1$_{NL4-3}$ proviral plasmid).

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

A. Definitions

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or can not occur, and that the description includes instances where said event or circumstance occurs and instances where it does not.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

In various aspects, the disclosed methods comprise a reporter system for nuclear migration based upon Bioluminesce Resonance Energy Transfer (BRET), which is analogous to the better-known FRET (Fluorescence Resonance Energy Transfer). In an aspect, the disclosed methods are based on the nucleus-specific and high-affinity interaction between two nuclear factors, LMO2 and Ldb1, which only interact in the nucleus. In an aspect, the disclosed methods comprise a HIV-1 Vpr N-terminally fused to EGFP and LMO2 protein. In an aspect, concomitantly, target cells are transduced to express a fusion protein, Ldb1-luciferase, e.g., the Nanoluc luciferase, which is a a high-efficiency luciferase. Without wishing to be bound by a particular theory, tagged virions carry the EGFP-LMO2-Vpr protein into the cells and nucleus. After this, the EGFP-LMO2-Vpr protein interacts with nuclear Lbd1-Nanoluc, exclusively in the nucleus, as this interaction only occurs in the nucleus. Thus, only true nuclear migration can be detected. Following protein-protein interaction, the addition of Nanoluc luminogenic substrate will then result in EGFP excitation and emission of the Ldb1-EGFP fusion protein. The signal can be measured quantitatively by photometer or flow cytometer. The disclosed methods has numerous advantages: (i) faster, signals are measured within hours of infection; (ii) convenient, signals are directly measured without the need for DNA extraction and quantification; (iii) more sensitive, nuclear migration in resting T cells can be measured within hours, and does not require T cell activation; (iv) direct, it is a direct measurement of the nuclear migration of PIC rather than a measurement of the surrogate DNA circles. In addition, given that the assay is performed in live cells, it will also allow monitoring nuclear migration over a time course. Furthermore, this reporter system would be amenable to high-throughput screening of HIV-1 nuclear migration inhibitors.

Integration of viral DNA is a decisive step in HIV infection and the establishment of viral latency. Successful integration requires three obligatory steps: viral entry, reverse transcription, and nuclear migration. For virology research, all of these steps need to be quantified. Notably, only two of them have fast, convenient, and quantitative assays—the BlaM- or Luciferase-based fusion assays (1, 2) and the quantitative real-time PCR (3). For measuring viral nuclear migration, a common method is to use the HIV 2-LTR circle as a surrogate, as it is only formed in the nucleus in the presence of host repair factors that mediate non-homologous end-joining (4). An alternative method requires nuclear fractionation, and a subsequent qRT-PCR of viral DNA in the nucleus (5). Both of these assays have limitations. At early times, only a small percentage of viral nuclear DNA forms 2-LTR circles, whereas following second round replication, 2-LTR circles accumulate in a significant amount. In particular, in HIV infection of resting CD4 T cells, the 2-LTR circle quantification is insensitive at early time points (before 12 hours), and frequently requires T cell activation and second round viral replication for quantification (5). In addition, certain drugs and viral mutations, such as the integrase inhibitors and the integrase mutation, lead to a dramatic aberrant accumulation of 2-LTR circles up to several hundreds' fold (6). As such, at best, the 2-LTR circle methodology is an inadequate correlative of viral nuclear migration. Alternatively, for measuring HIV early nuclear migration in resting CD4 T cells, nuclear fractionation is often used (5, 7). The method is tedious, requires multiple fractionation controls, and there is a significant risk of contamination from the cytoplasmic compartment. Additionally, both assays are not amenable to high-throughput screening.

The disclosed nuclear migration reporter assay is predicated on the high-affinity interaction of two nuclear proteins, LMO2 and Ldb1 (8, 9). LMO2 and Ldb1 canonically form multimeric transcription factor complexes in the nucleus that mediate transactivation or repression of target genes (10). Specifically, viral Vpr can be fused to LMO2 and EGFP. The resulting protein is designated as EGFP-LMO2-Vpr. The proper processing and virion incorporation of Vpr fusion proteins have been previously characterized for tracking viral entry and nuclear migration (1, 11, 12). This EGFP-LMO2-Vpr fusion protein can be provided in trans with the proviral plasmid, pNL4-3, to produce viral particles carrying the fusion protein. Simultaneously, target cells can be transduced to express the BRET donor, Ldb1-Nanoluc (or Ldb1-NL). As such, after infection and nuclear migration in the target cells, association of EGFP-LMO2-Vpr with Ldb1-NL can occur exclusively in the nucleus. Upon addition of luminogenic Nanoluc substrate, the Ldb1-NL protein will produce light capable of exciting EGFP-LMO2-Vpr. Emission from EGFP, the result of BRET, will be a quantitative readout of nuclear migration. Due to the nucleus-specific distribution of these proteins, only true nuclear migration can be detected.

The use of Vpr fusion protein ensures nuclear localization. The use of Nanoluc as the BRET donor has additional advantages (13). For instance, Nanoluc exhibits 100-150-fold high activity than the more-conventional Renillia or firefly luciferases. This, along with the virion incorporation of Vpr, will ensure maximum sensitivity. More broadly, the use of BRET offers other advantages. Unlike FRET, where laser excitation wavelengths can "bleed into" the emission channel, BRET requires no extrinsic excitation laser. This reduces background and increases sensitivity. Additionally, because the resultant product is EGFP emission, this assay will allow for nuclear migration quantification in fluorescent microscopy, flow cytometry, and standard fluorometry. This unique combination of factors makes this approach highly innovative, and ensures that the resultant reporter assay will be extremely sensitive, specific, quantitative, and have broad utility in the field of retrovirology research.

B. References

1. Cavrois M, De Noronha C, Greene W C. A sensitive and specific enzyme-based assay detecting HIV-1 virion fusion in primary T lymphocytes. Nat Biotechnol. 2002; 20(11):1151-4.
2. Gerlach L O, Skerlj R T, Bridger G J, Schwartz T W. Molecular interactions of cyclam and bicyclam non-peptide antagonists with the CXCR4 chemokine receptor. J Biol Chem. 2001; 276(17): 14153-60.
3. Butler S L, Hansen M S, Bushman F D. A quantitative assay for HIV DNA integration in vivo. Nat Med. 2001; 7(5):631-4.
4. Kilzer J M, Stracker T, Beitzel B, Meek K, Weitzman M, Bushman F D. Roles of host cell factors in circularization of retroviral dna. Virology. 2003; 314(1):460-7.
5. Yoder A, Yu D, Dong L, Iyer S R, Xu X, Kelly J, et al. HIV envelope-CXCR4 signaling activates cofilin to overcome cortical actin restriction in resting CD4 T cells. Cell. 2008; 134(5):782-92.
6. Engelman A, Englund G, Orenstein J M, Martin M A, Craigie R. Multiple effects of mutations in human immunodeficiency virus type 1 integrase on viral replication. J Virol. 1995; 69(5):2729-36.
7. Wang W, Guo J, Yu D, Vorster P J, Chen W, Wu Y. A dichotomy in cortical actin and chemotactic actin activity between human memory and naive T cells contributes to their differential susceptibility to HIV-1 infection. J Biol Chem. 2012; 287(42):35455-69.
8. Deane J E, Mackay J P, Kwan A H, Sum E Y, Visvader J E, Matthews J M. Structural basis for the recognition of ldbl by the N-terminal LIM domains of LMO2 and LMO4. Embo J. 2003; 22(9):2224-33.
9. Ryan D P, Duncan J L, Lee C, Kuchel P W, Matthews J M. Assembly of the oncogenic DNA-binding complex LMO2-Ldb1-TAL1-E12. Proteins. 2008; 70(4):1461-74.
10. Curtis D J, McCormack M P. The molecular basis of Lmo2-induced T-cell acute lymphoblastic leukemia. Clin Cancer Res. 2010; 16(23):5618-23.
11. McDonald D, Vodicka M A, Lucero G, Svitkina T M, Borisy G G, Emerman M, et al. Visualization of the intracellular behavior of HIV in living cells. J Cell Biol. 2002; 159(3):441-52.
12. Campbell E M, Perez O, Melar M, Hope T J. Labeling HIV-1 virions with two fluorescent proteins allows identification of virions that have productively entered the target cell. Virology. 2007; 360(2):286-93.
13. Hall M P, Unch J, Binkowski B F, Valley M P, Butler B L, Wood M G, et al. Engineered luciferase reporter from a deep sea shrimp utilizing a novel imidazopyrazinone substrate. ACS Chem Biol. 2012; 7(11):1848-57.
14. Li C, Wen A, Shen B, Lu J, Huang Y, Chang Y. FastCloning: a highly simplified, purification-free, sequence- and ligation-independent PCR cloning method. BMC Biotechnol. 2011; 11:92. PMCID: 3207894.
15. Guo J, Wang W, Yu D, Wu Y. Spinoculation triggers dynamic actin and cofilin activity facilitating HIV-1 infection of transformed and resting CD4 T cells. J Virol. 2011; 85(19):9824-33.
16. Cameron P U, Saleh S, Sallmann G, Solomon A, Wightman F, Evans V A, et al. Establishment of HIV-1 latency in resting CD4+ T cells depends on chemokine-induced changes in the actin cytoskeleton. Proc Natl Acad Sci USA. 2010; 107(39):16934-9.
17. Unutmaz D, KewalRamani V N, Marmon S, Littman D R. Cytokine signals are sufficient for HIV-1 infection of resting human T lymphocytes. J Exp Med. 1999; 189(11): 1735-46.

C. Examples

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. BRET-Based LMO2-LDB1 Nuclear Migration Assay

Figure 1B:
FIG. 1B shows a schematic representation of a representative disclosed recombinant DNA construct comprising a CMV promotor (designated as "CMV" in the figure) operably linked to a coding region encoding a fusion protein comprising a nucleotide sequence encoding a luciferase polypeptide (designated as "NL" in the figure) inframe with a nucleotide sequence encdoing a LMO2 polypeptide inframe with a nucleotide sequence encoding a Vpr polypeptide, with the coding region operably linked to a polyadenylation signal sequence (designated as "pA" in the figure).
Figure 1C:
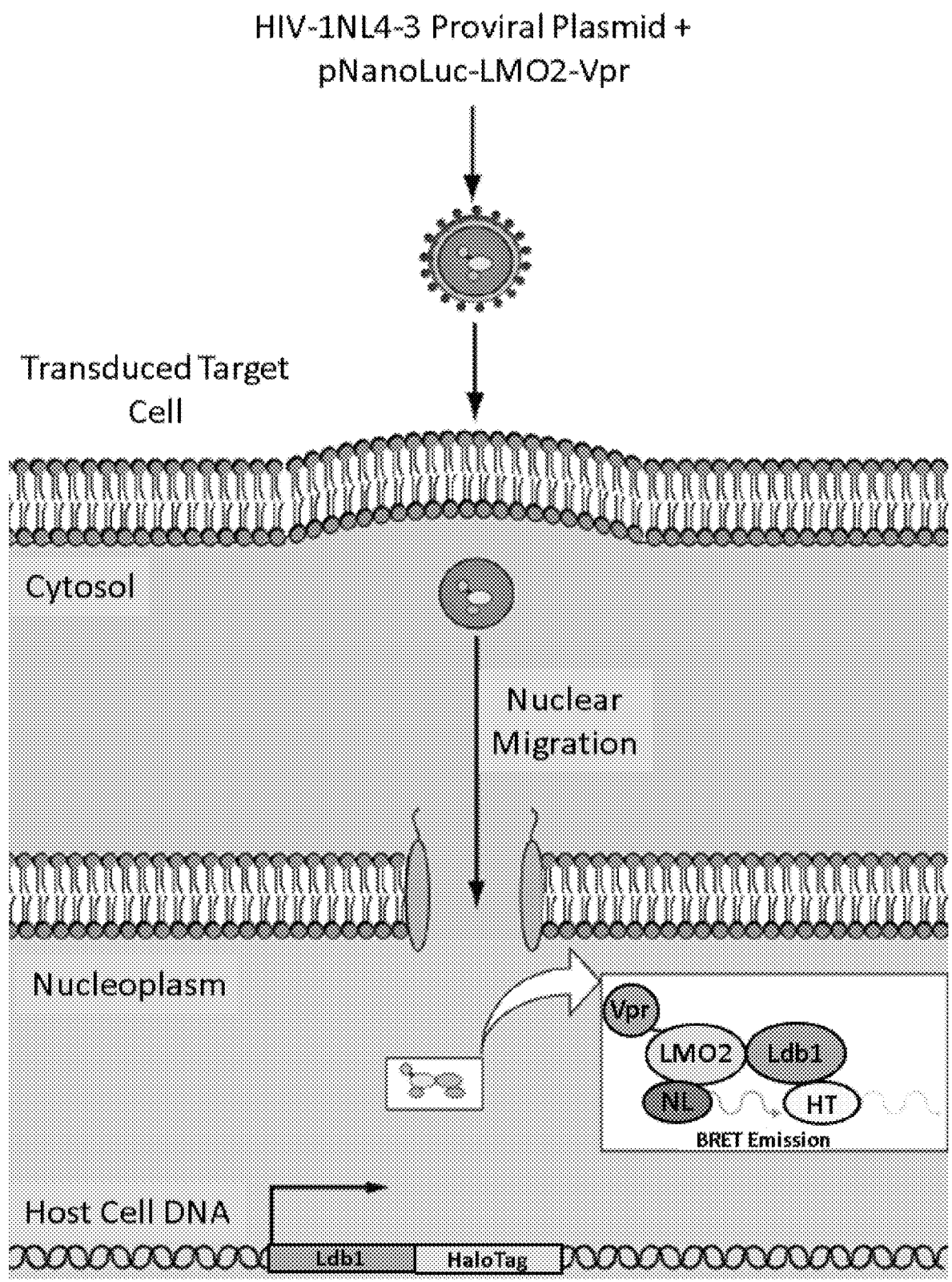
FIG. 1C shows a schematic representation of a disclosed assay method. Briefly, a recombinant DNA construct for a fusion protein comprising a luciferase polypeptide, a LMO2 polypeptide, and a Vpr polypeptide (designated as "NanoLuc-LMO2-Vpr") is provided in trans during virion production from a proviral plasmid (designated as "HIVNL4-3 Proviral Plasmid" in the figure), resulting in the packaging of the reporter protein. Infection of a target cell results in nuclear trafficking of the Vpr fusion protein, whereupon it can interact with the BRET acceptor fusion protein comprising a LDB1 polypeptide and a reporter polypeptide, HaloTag (designated as "Ldb1-HaloTag" in the figure), in the target cell, resulting in a BRET emission, which can be detected and is a measure of the nuclear localization of the Vpr.

A pair of vectors were developed to determine interactions of the two fusion constructs using confocal microscopy with FRET detection. The vectors, designated as pNL- LMO2-Vpr (see FIG. 1B) and pLDB1-HT. The pEGFP-LMO2-Vpr vector comprises a promoter operably linked to a nucleotide sequence encoding a fusion protein comprising an luciferase polypeptide, a LMO2 polypeptide, and a Vpr polypeptide. The pLDB1-HT vector comprises a promoter operably linked to a nucleotide sequence encoding a fusion protein comprising an LDB1 polypeptide and a HaloTag polypeptide. The overall assay scheme is diagrammed in FIG. 1C. Data obtained using these constructs are shown in FIGS. 2A-2D.

Figure 2D:
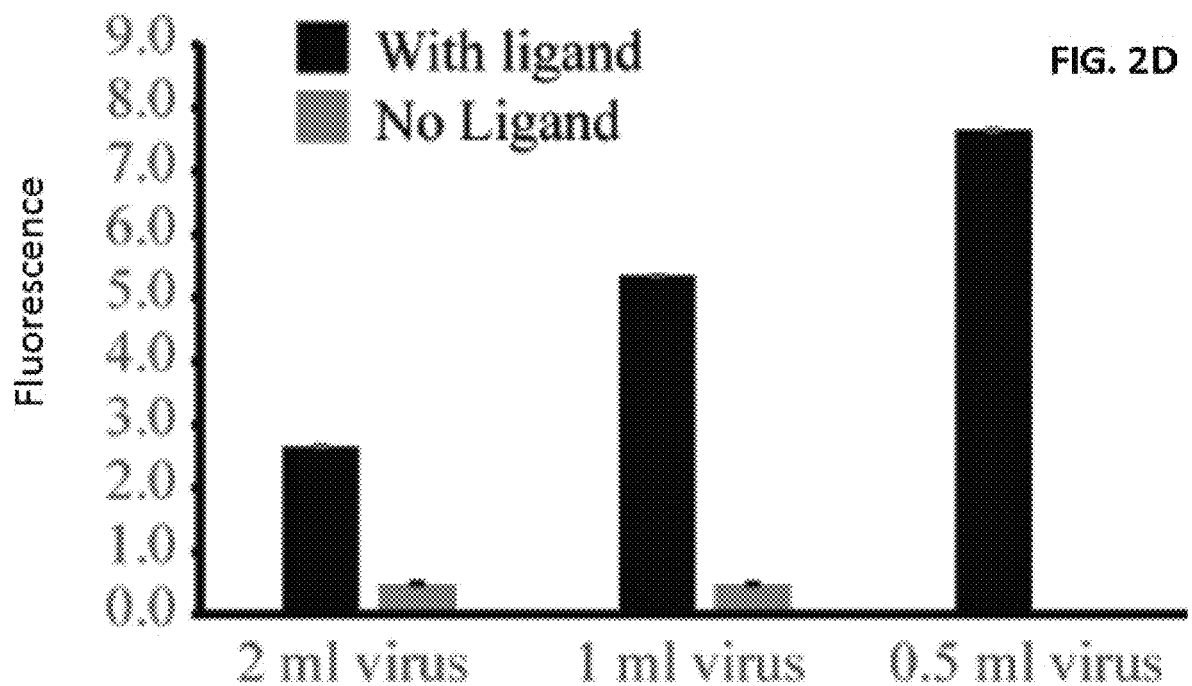

The disclosed assay utilizes the interaction of a BRET donor, such as a fusion protein comprising a luciferase polypeptide fused to an interactor, LMO2, and a viral protein, Vpr. Moreover, the disclosed utilizes the expression of a nucleus localized BRET acceptor, such as a fusion protein comprising a reporter, e.g., HaloTag or a GFP, and the other interacting partner, Ldb1, in the target cell. Though LMO2 and Ldb1 are known to interact in vivo, whether the above-mentioned fusion proteins interact was not known. The data shown in FIGS. 2A-2D, using FRET and BRET, demonstrate that the fusion constructs are able to interact. For the FRET experiment, HEK293T cells were transfected with pEGFP-LMO2-Vpr and pCEP4-Ldb1-mCherry. As shown in FIG. 2A, FRET was observed in these cells in cotransfection. Further studies demonstrated that FRET was not observed when either pEGFP-LMO2-Vpr or pCEP4-Ldb1-mCherry were transfected alone. A BRET interaction experiment using pNL-LMO2-Vpr and pLdb1-HaloTag, which was also performed in HEK293T cells. As shown in FIG. 2B, only when the fluorescent HaloTag ligand was provided was BRET observed.

For the nuclear migration assay to perform as expected, the viral particle needs to transduce enough of the BRET donor, NanoLuc-LMO2-Vpr, to be detected. Additionally, enough of the reporter needs to localize to the nucleus to observe BRET. As such, HEK293T cells were transfected with the BRET acceptor, pLdb1-HaloTag, and either incubated overnight with DMSO or the HaloTag fluorescent ligand. Cells were then subsequently infected with 2 ml, 1 ml, or 0.5 ml of virus carrying NanoLuc-LMO2-Vpr. Further studies demonstrated that sufficient NanoLuc-LMO2-Vpr was virally transduced to generate a luminescent signal 3-4 orders of magnitude above background. Additionally, as shown in FIG. 2C, upon infection, BRET was observed between the donor-acceptor pair. For the control, BRET was not observed when the fluorescent HaloTag ligand was not provided.

Figure 3A:
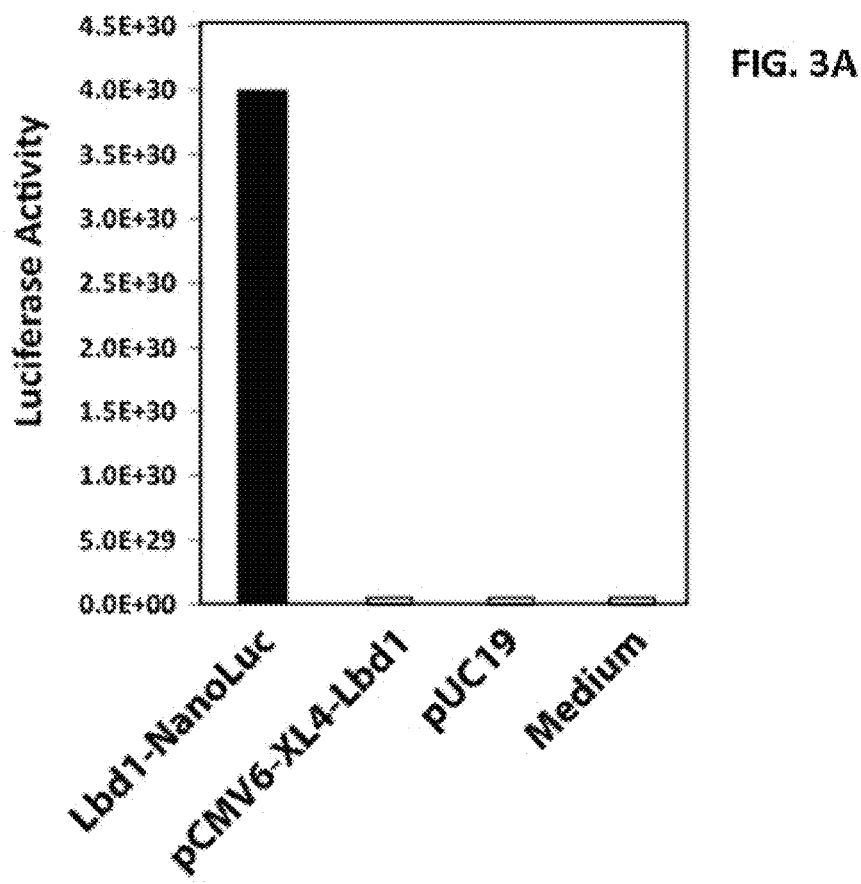
FIGS. 3A-3D show representative data pertaining to the expression, intracellular stability, and nuclear localization of disclosed fusion constructs. The fusion constructs are EGFP-LMO2-Vpr (encoded on a recombinant DNA construct designated as pEGFP-LMO2-Vpr in the figure) and LDB1-Luciferase (encoded on a recombinant DNA construction designated as pCMV6-XL4-Ldb1-NanoLuc in the figure). The recombinant DNA constructs were trasnsfected into HEK293 T cells by Lipofectamine 2000 transfection (Invitrogen). In brief, 4 µg of pCMV6-XL4-Ldb1-NanoLuc or pEGFP-LMO2-Vpr were transfected into HEK293T cells in each well of a 6-well plate. At 48 hours post-transfection, samples were taken for luminometric, flow cytometric analysis, or fluoresecent microscopy. For NanoLuc luminometric analysis, high-levels of luciferase reading from pCMV6-XL4-Lbd1-NanoLuc were observed (see FIG. 3A). The EGFP-LMO2-Vpr was observed by flow cytometry (FIGS. 3B and 3C). Fluoresecent microscopy confirmed that the EGFP-LMO2-Vpr expression was exclusively nuclear (FIG. 3D).
Figure 3B:
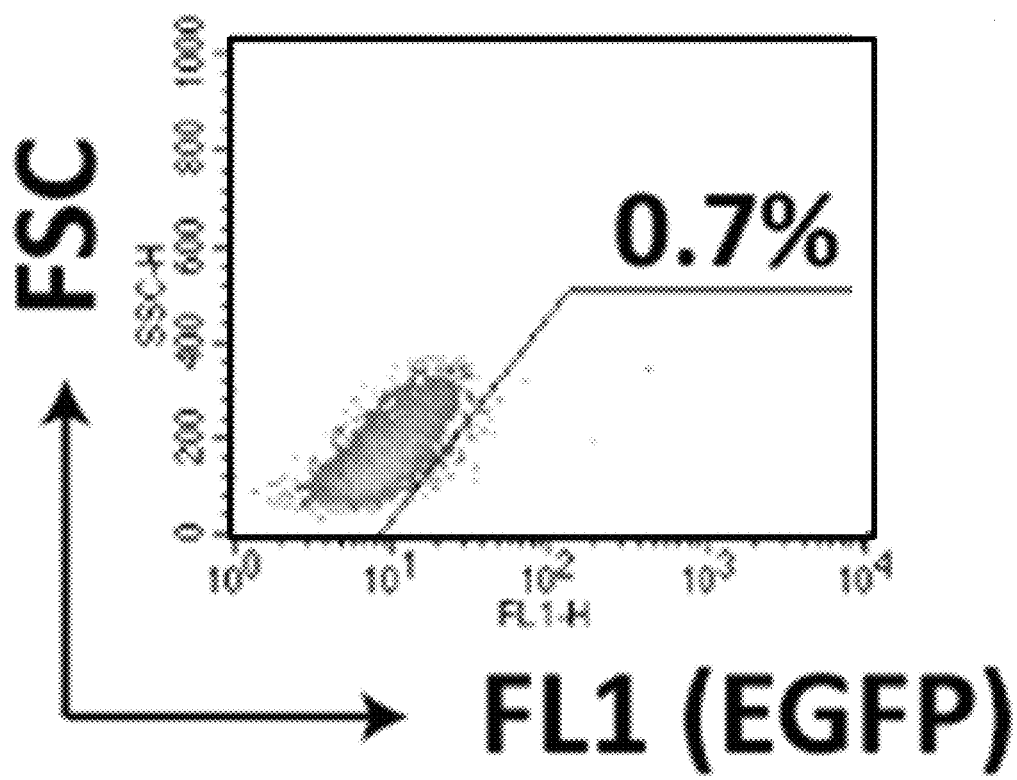
Figure 3C:
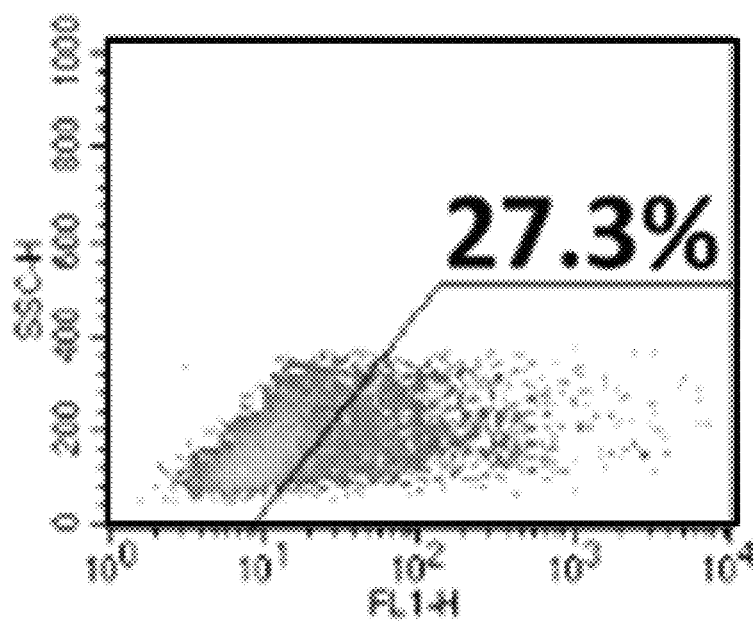
Figure 3D:
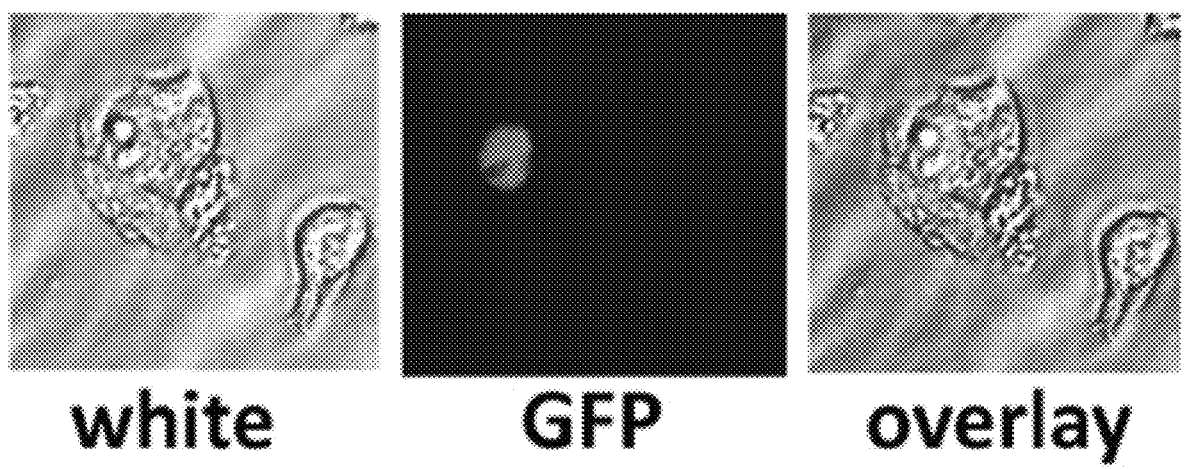
Figure 4C:
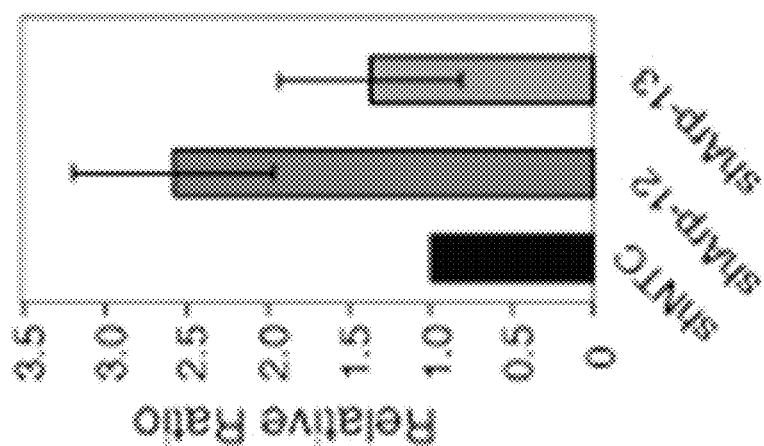
FIGS. 4A-4E show representative data demonstrating that Arp3 knockdown diminishes HIV-1 infection and viral nuclear migration. Briefly, Arp3 knockdown in shArp-12, shArp-13, and the control shNTC cells was analyzed by Western Blot (see FIG. 4A). shArp-12, shArp-13, and shNTC cells were infected with HIVNL4-3 to monitor viral replication by p24 release (see FIG. 4B). Viral etnry into shArp-12, shArp-13, and shNTC was measured with a Nef-luciferase-based entry assay (see FIG. 4C). shArp-12, shArp-13, and shNTC cells were infected with a single-cycle HIV-1(Env) that was pseudotyped with HIV-1 gp160. Cells were infected for 2 hours, washed, and then taken at different time points for PCR quantification of viral DNA (see FIG. 4D). Viral 2-LTR circles following HIV infection at 48 hours were also measured (see FIG. 4E).
Figure 4B:
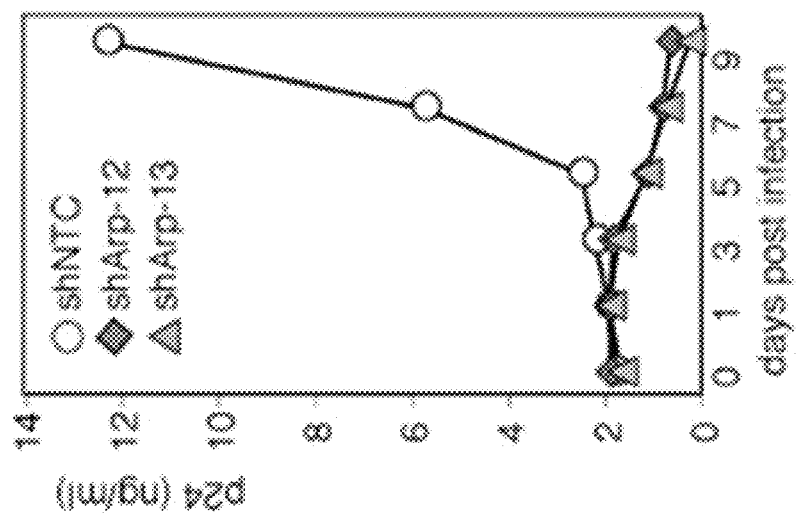
Figure 4A:
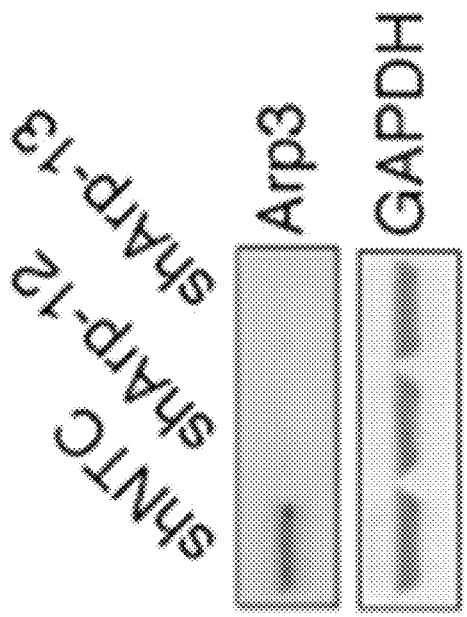
Figure 4E:
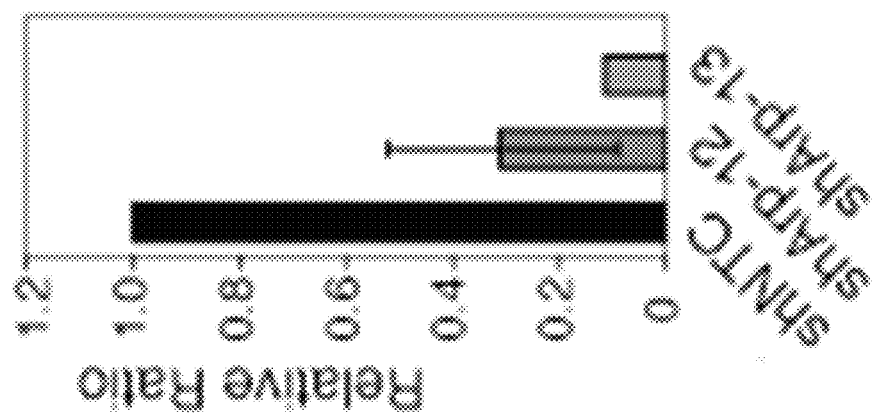
Figure 4D:
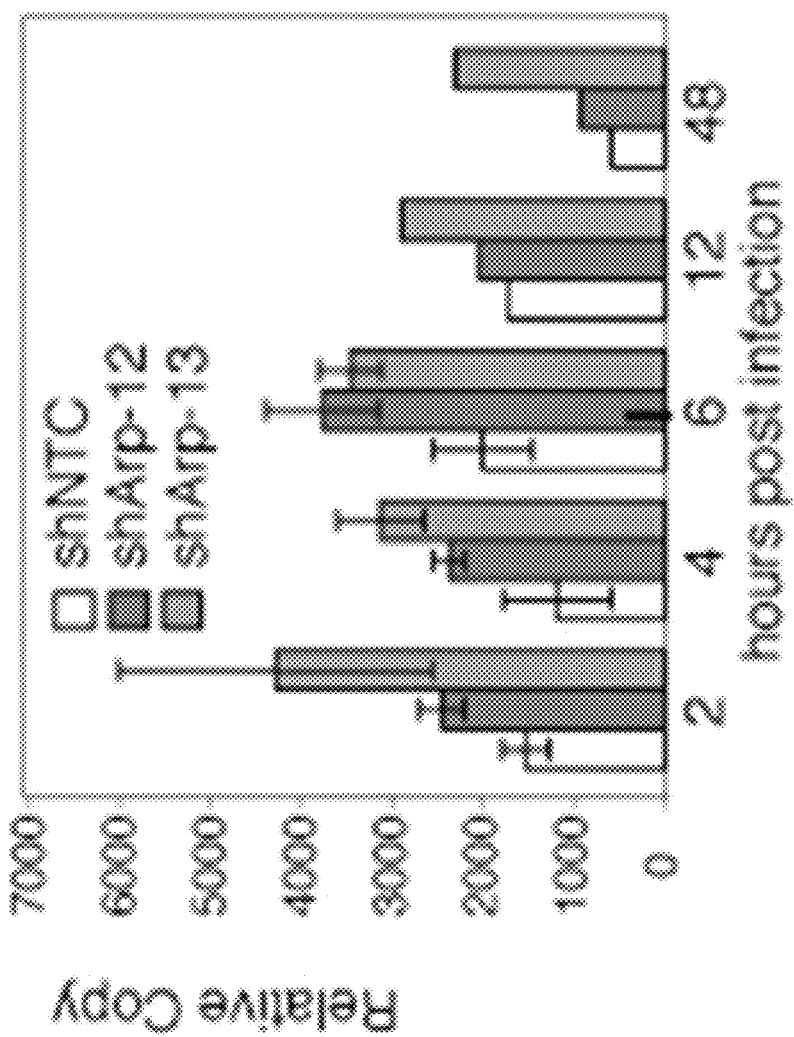
Figure 5A:
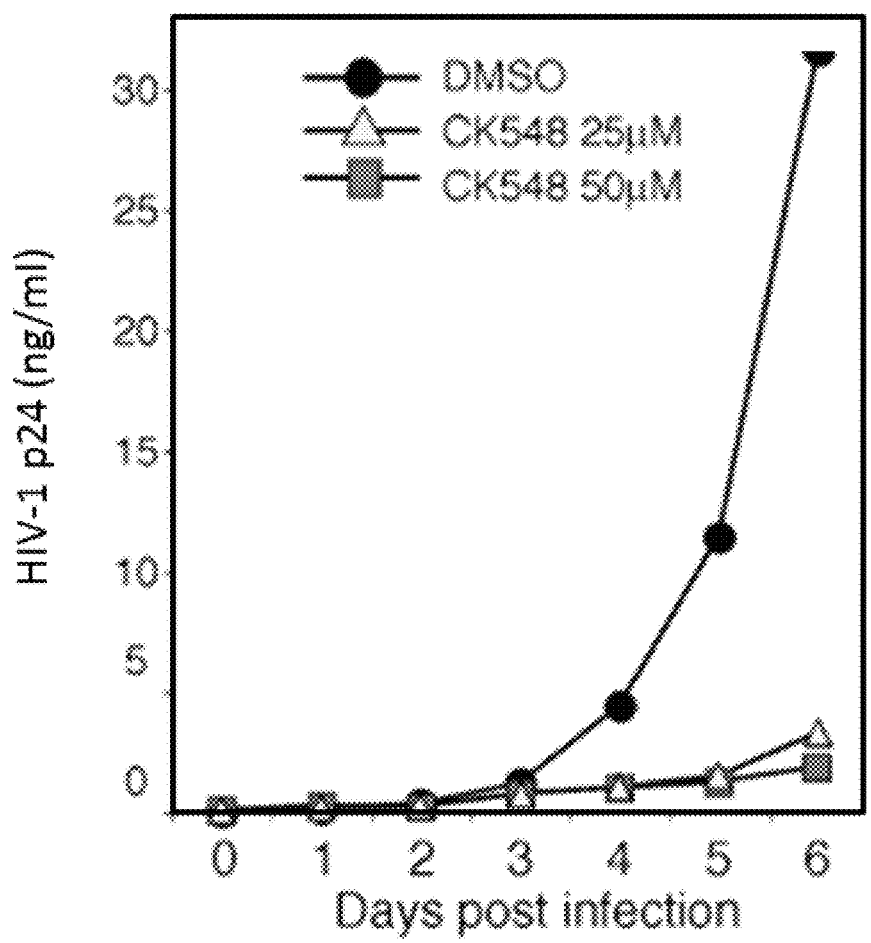
FIGS. 5A-5D show representative data demonstrating that CK548 inhibits HIV-1 infection and viral nuclear migration. Briefly, CEM-SS T cells were pre-treated with DMSO or CK548 for 1 hour, and then infected with HIV-1NL4-3. Viral replication was measured by p24 release (see FIG. 5A). Drug cytotoxicity was meaured in CK548-treated and infected cells by PI staining and flow cytometry (see FIG. 5B). Shown is the percentage of PI-positive cells. No drug cytotoxicity was detectable at 50 µM and below CEM-SS T cells were pretreated with DMSO or CK548 for 1 hour, and then infected with a single-cycle HIV-1(Env) that was pseudotyped with HIV-1 gp160. Cells were infected for 2 hours, washed, and cultured in the presence of the drug for 48 hours. Total cellular DNA was extracted at 48 hours post infection and then PCR-amplified to quantify viral DNA (for results see FIG. 5C). Viral 2-LTR-circles were also measured (see FIG. 5D). The relative ratio of 2-LTR circles to viral total DNA was also plotted. "ND" in the figure indicates that the signal was not detectable.
Figure 5B:
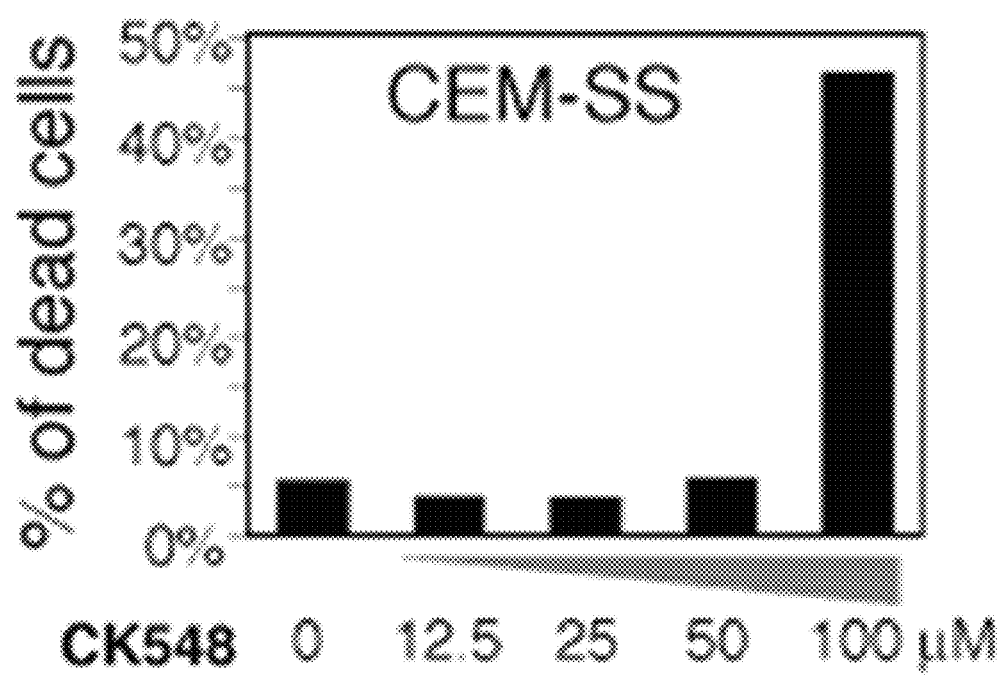
Figure 5C:
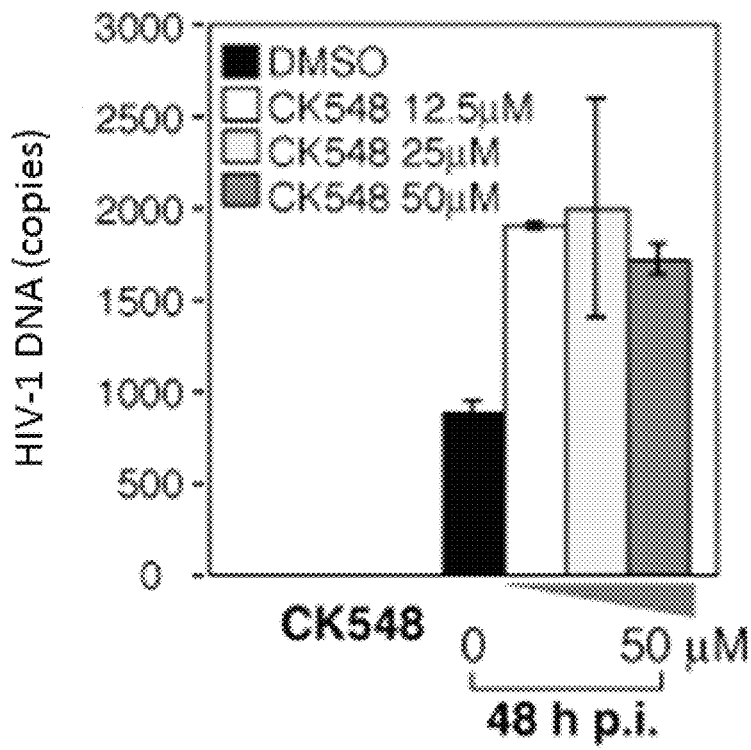
Figure 5D:
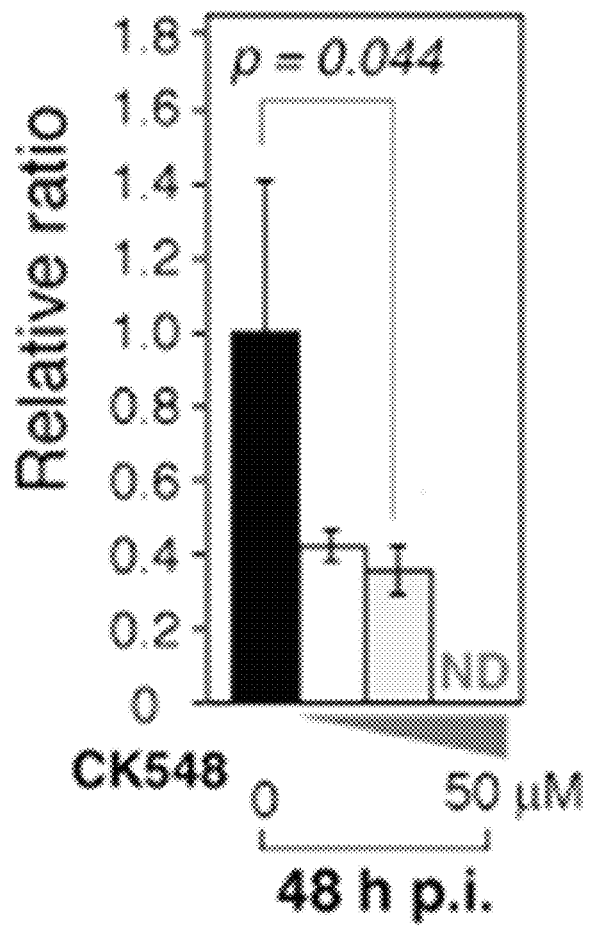

2. Expression, Intracellular Stability, and Nuclear Localization of the Two Reporter Proteins In order to determine the expression, intracellular stability, and nuclear localization of the two reporter proteins as described above, pEGFP-LMO2-Vpr and pCMV6-XL4-Ldb1-NanoLuc were constructed. Both expression vectors were trasnfected into HEK293 T cells by Lipofectamine 2000 transfection (Invitrogen). In brief, 4 µg of pCMV6-XL4-Ldb1-NanoLuc or pEGFP-LMO2-Vpr were transfected into HEK293T cells in each well of a 6-well plate. 48 hours post-transfection, samples were taken for luminometric, flow cytometric analysis, or fluoresecent microscopy. For NanoLuc luminometric analysis, we observed high-levels of luciferase reading from pCMV6-XL4-Lbd1-Nano-Luc (FIG. 3A). We also observed EGFP expression of pEGFP-LMO2-Vpr by flow cytometry (FIG. 3B). Fluoresecent microscopy confirmed that the EGFP expression is exclusively nuclear (FIG. 3C).

3. Vector Construction

Cloning was performed using a PCR-based cloning protocol as described by Li (14). In brief, ligation-independent cloning will be performed after high-fidelity PCR amplification of the vector and insert from plasmids, followed by mixing the two reactions. DpnI treatment will be used to remove contaminating plasmids before E. coli transformation. Nanoluc (Promega) will cloned into pCMV6-XL4-Ldb1 (OriGene) using the following primers: NanoLuc Forward-5' GTCACAGGCCTCCCAGATGGTCTTCA-CACTCGAA 3'; NanoLuc Reverse-5' CACAGCAGGGC-CTTTTATTACGCCAGAATGCGTTC 3'; Ldb1 Forward-5' TAAAAGGCCCTGCTGTG 3'; Ldb1 Reverse-5' CTGGGAGGCCTGTGAC 3'. Similarly, LMO2 was cloned from pCMV6-XL5-LMO2 (OriGene) into pEGFP-Vpr (NIH AIDS Reagent Program) using the following primers: LMO2 Forward-5' GATCTCGAGCTCAAGCTTATGTC-CTCGGCCATCG 3'; LMO2 Reverse-5' GTCT-TCTGGGGCTTGTTCTATCATCCCATTGATCTTAGT 3'; pEGFP-Vpr Forward-5' GAACAAGCCCCAGAAGAC 3'; pEGFP-Vpr Reverse-5' AAGCTTGAGCTCGAGATC 3'. The Ldb1-NL fusion construct will further be cloned in the lentiviral vector, pLKO.1-Puro for lentiviral particle production.

4. Viral Particle Construction

Recombinant, HIV viral particles are produced by co-transfection of pEGFP-LMO2-Vpr, which will express the Gag-Pol-LMO2-NL polyprotein, and pNL4-3 proviral plasmid. The resulting viral particles will be competent for infection in target cells and will carry the EGFP-LMO2-Vpr fusion protein.

For producing viral particles for lentiviral transduction of target cells, pLKO.1-Puro-Ldb1-NL will be cotransfected with the packaging plasmid, pCMV☐8.2, and a vector expressing the HIV envelope protein gp160 or pHCMV-G, which expresses the VSV-G glycoprotein envelope. The resulting virus particles will be concentrated and used to infect target cells.

5. Reporter Cell Line Construction

Target cells will be tranduced with the vLKO.1-Puro-Ldb1-NL particles. Approximately 2 days post-infection, cells will be selected in puromycin to remove non-transduced cells. The transduced target cells will be ready to use following selection.

6. Assay Characterization

Ldb1-NL-transduced target cells will be first infected with wt HIV-1NL4-3. Nuclear migration will be measured by 3 different assays. For nuclear fractionation and 2-LTR circules, lysates will be taken at 2, 4, 6, 12, 18, and 24 hours post-infection. Subsequently, lysates will be subjected to fractionation or direct extraction to measure nuclear viral DNA and 2-LTR circle DNA, respectively. For comparison with BLNMA, target cells will be similarly infected with HIVNL4-3 (EGFP-LMO2-Vpr), and flow cytometry samples will be taken at the same time points. To induce luminescence and BRET, the Nanoluc substrate will be loaded into the flow cytometry samples immediately prior to analyzing the sample, which will allow analysis of EGFP-emitting cells in which nuclear migration has occurred.

To verify the specificity of this assay further, this reporter assay will be performed in the presence of nuclear migration-promoting conditions and agents, such as spinoculation (15), or the chemokines CCL-19 and CCL-21 (16). These chemokines have been previously shown to upregulate nuclear migration of resting CD4 T cells (16). For measuring nuclear migration in resting CD4 T cells, cells will be cultured in IL-7, and then transduced with the vLKO.1-Puro-Ldb1-EGFP vector. Culturing CD4 T cells in IL-7 has been known to effectively permit them to be transduced by lentiviral vectors for gene expression (17).

The nuclear migration assay was performed in two CEM-SS-based cells, shArp-12 and shArp-13, which we recently constructed. In both shArp-12 and shArp-13, the actin branching factor Arp3 was stably knockdown (80% knockdown). The cloned cells exhibited a marked defect in nuclear migration, with little impact on reverse transcription (FIGS. 4A-4D). As indicated, 2-LTR circles were used as a correlative of nuclear entry in our characterization of shArp-12 and shArp-13, which had a dramatic reduction of 2-LTR circles. We will re-measure the nuclear entry defect by BLNMA. In addition, recently, we also found that a novel Arp2/3 inhibitor, CK548, dramatically inhibited HIV nuclear migration while stimulating HIV DNA synthesis (FIGS. 5A-5D). We will also perform BLNMA to confirm the phenotype.

7. Assay Results

Figure 6:
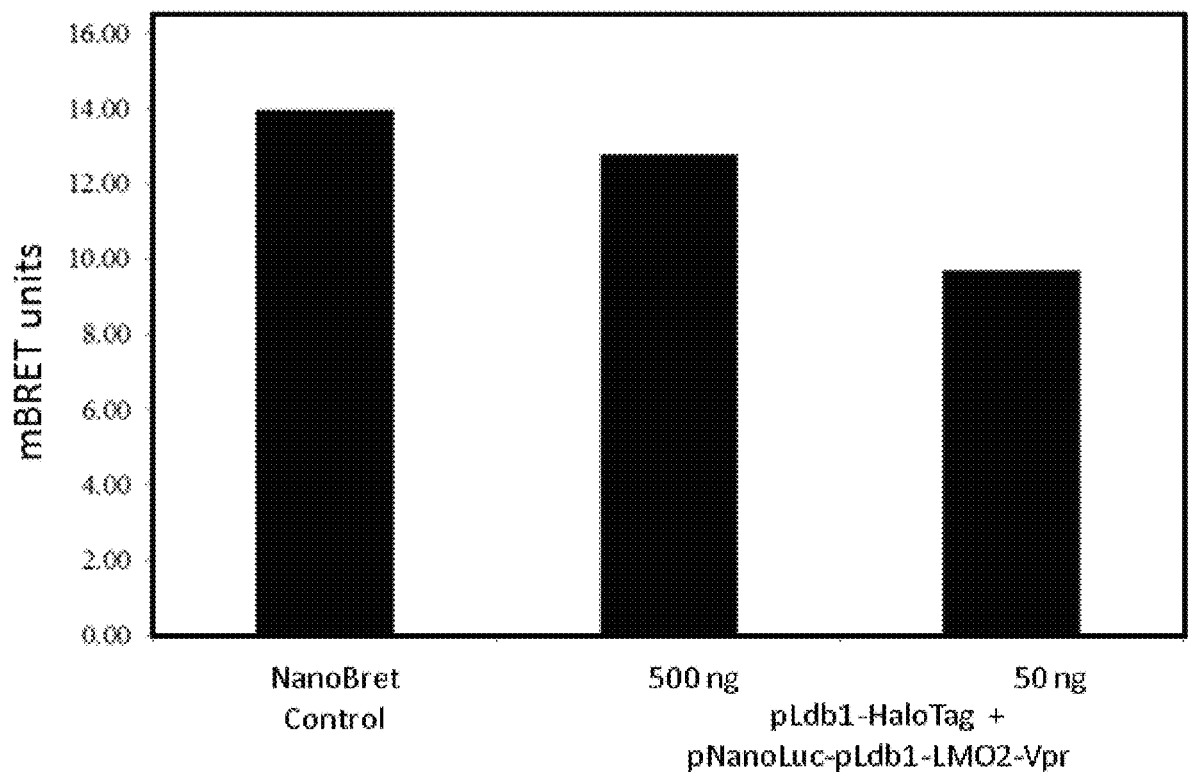
FIG. 6 shows representative data demonstrating that the use of a pair of disclosed fusion constucts in a disclosed method provides a functional BRET pair. The two fusion constructs were: a) a luciferase-LMO2-vpr fusion construct (designated as pNanoluc-LMO2-Vpr in the figure); and b) a LDB1-HaloTag fusion construct (designated as pLdb1-HaloTag in the figure). Briefly, pNL-LMO2-Vpr and pLdb1-HT were co-transfected into HEK293T cells with either 500 or 50 ng of the pNL-LMO2-Vpr vector. For comparison, 4 µg of pNanoBRET control plasmid was also transfected. mBRET Units were calculated by subtracting the BRET ratio from the acceptor without ligand from the BRET ratio of the acceptor with ligand (618 ligand) and multiplying by 1000.
Figure 7:
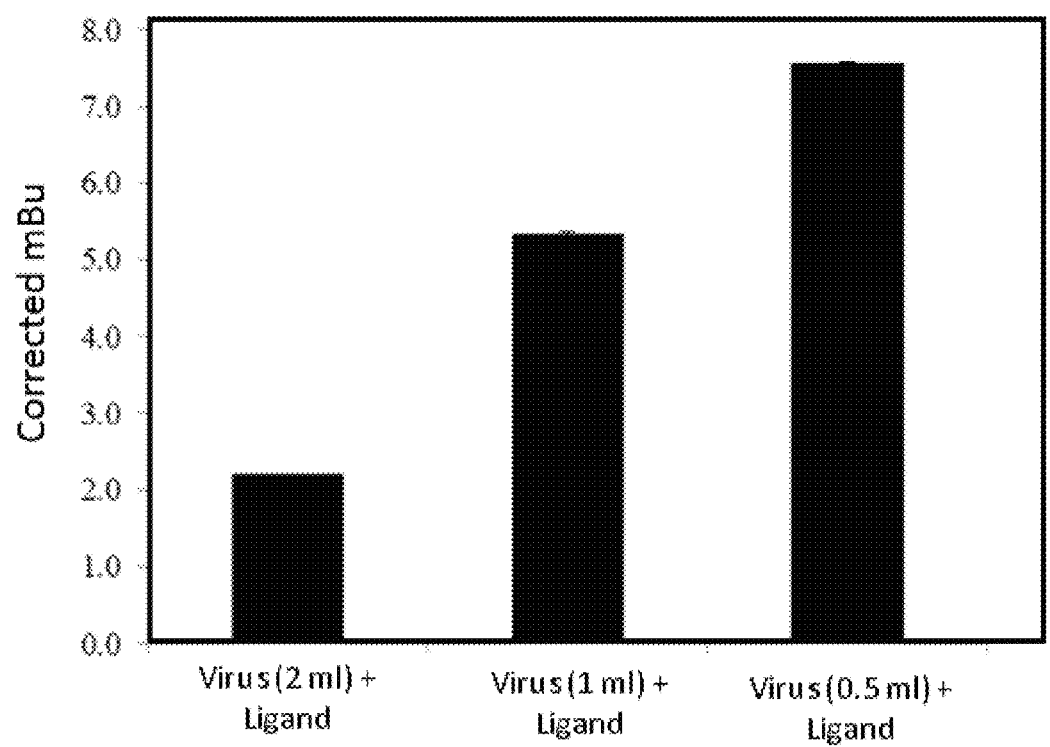
FIG. 7 shows representative data demonstrating that infection of cells with disclosed recombinant viral particle can induce BRET. HEK293T cells were transfected with pLdb1-HT (comprising a recombinant DNA construct comprising a promoter operably linked to a nucleotide sequence encoding a fusion construct comprising LDB1 and HaloTag). After 24 hours post-transfection, the transfected cells were infected with 2, 1, or 0.5 ml of virus particles comprising a fusion construction comprising a luciferase polypeptide, a LMO2 polypeptide, and a Vpr polypeptide. The data are plotted in terms of corrected mBRET units; mBRET units are as defined for FIG. 6.

The BRET pair function in co-transfection of the two plasmids, pNanoluc-LMO2-Vpr and pLdb1-HaloTag, was tested and compared to a NanoBRET control vector from Promega (FIG. 6). As shown, the BLNMA BRET pair compared favorably to the NanoBRET control. Further aspects of the assay were demonstrated using HIVNL4-3 (VSV-G, Nanoluc-LMO2-Vpr) created virions, pseudotyped with the VSV-G envelope and carrying the Nanoluc-LMO2-Vpr protein. These were used to infect HEK293T cells transfected with pLdb1-HaloTag. As shown in FIG. 7, infection-induced BRET was readily detected. Collectively, these data indicate the assay may work as outlined above.

Identification of CCL-19/CCL-21-mediated upregulation of nuclear migration, and downregulation in shArp-12, -13 and CK548-treated cells, indicates the assay is specific to nuclear migration events. More specifically, these particular treatments reflect examples of nuclear migration modulation, and would indicate if the nuclear migration reporter assay is sensitive and quantitative enough to detect changes in nuclear migration. The CK548 treatment demonstrates the utility of the disclosed method for potential drug screening of nuclear migration inhibitors.

The transduction of target cells with vLKO.1-Puro-Ldb1-NL vector is one approach for routinely used HIV target cell lines. This approach particularly fits the purpose of drug screening, where stable cell lines carrying Ldb-NL can be constructed. For resting CD4 T cells, the vector can also be used for transduction following cytokine culturing of resting CD4 T cells (17). However, there are situations where resting CD4 T cells will be directly infected. For this purpose, the disclosed method can be readily modified by using two differently labeled particles: one carrying EGFP-LMO2-Vpr, as described above, the other carrying NL-Ldb1-Vpr. The two particles will be assembled separately and mixed with at 1:1 ratio, and then used for infection. Infected cells will have LMO2-Ldb1 interaction in the nucleus following nuclear migration.

The data shown herein suggest that in some apsects, the recombinant virus particle, rather than the cell, should carry a luciferase reporter, as a lower NanoLuc input signal typically increases the BRET ratio. In an aspect, the cell should harbor the fluorescent BRET acceptor. In a further aspect, the fluorescent reporter should be red-shifted. For example, it may be preferable in some aspects, to use a reporter such as HaloTag, which can be loaded with a BRET-optimized fluorescent ligand (excitation maximum at 618 nm).

8. BRET Based HIV-1 Nuclear Migration Assay

Disclosed herein are HIV-1 nuclear migration assays based on the protein:protein interaction of the nuclear factors LMO2 and Ldb1. LMO2 and Ldb1 are scaffolding proteins that are constituents of a multicomponent transcriptional complex and interact with each other in the nucleus. These two nuclear factors can be utilized in the HIV-1 nuclear migration assay by creating two separate fusion proteins that, following HIV infection, interact with one another in the nucleus to generate a bioluminescent resonance energy transfer (BRET) signal. The two fusion proteins utilized to generate this signal are Nanoluc-LMO2-Vpr and Ldb1-Halotag. The Nanoluc-LMO2-Vpr fusion protein can be incorporated within the virion of wild-type HIV (NL4-3), and either HeLa JC53 or A3R5.7 cells that are susceptible to infection by HIV-1 will constitutively express the Ldb1-Halotag fusion protein. The signal generated through the interaction of these fusion proteins is based upon the NanoBRET technology developed by Promega and requires that the Nanoluc and Halotag components of the fusion proteins be in close proximity to one another to generate the assay signal.

Figure 8:
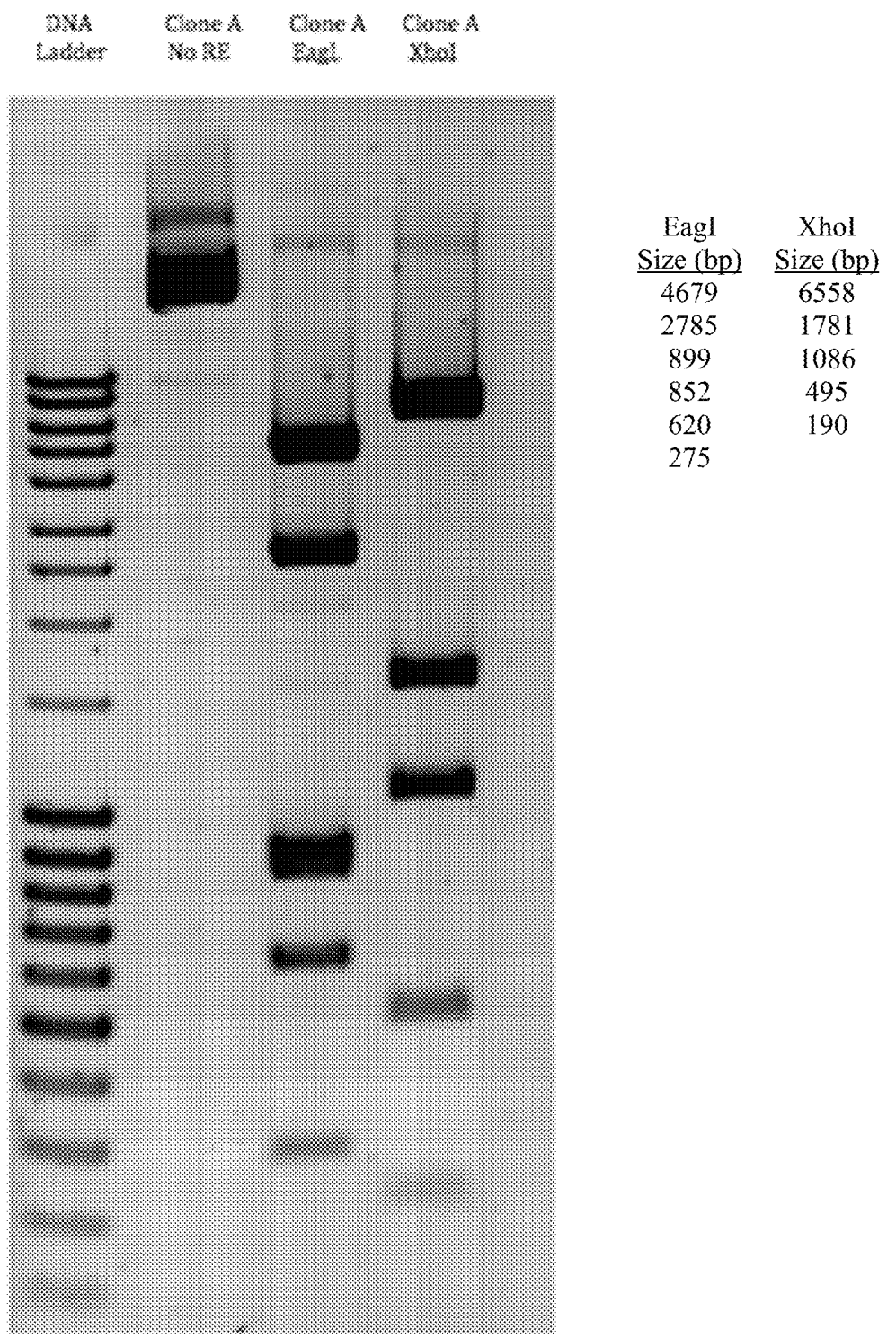
FIG. 8 shows confirmation of pLKO.1 MCS Puro Lbd1-HT by restriction enzyme digest and agarose gel electrophoresis.
Figure 9A:
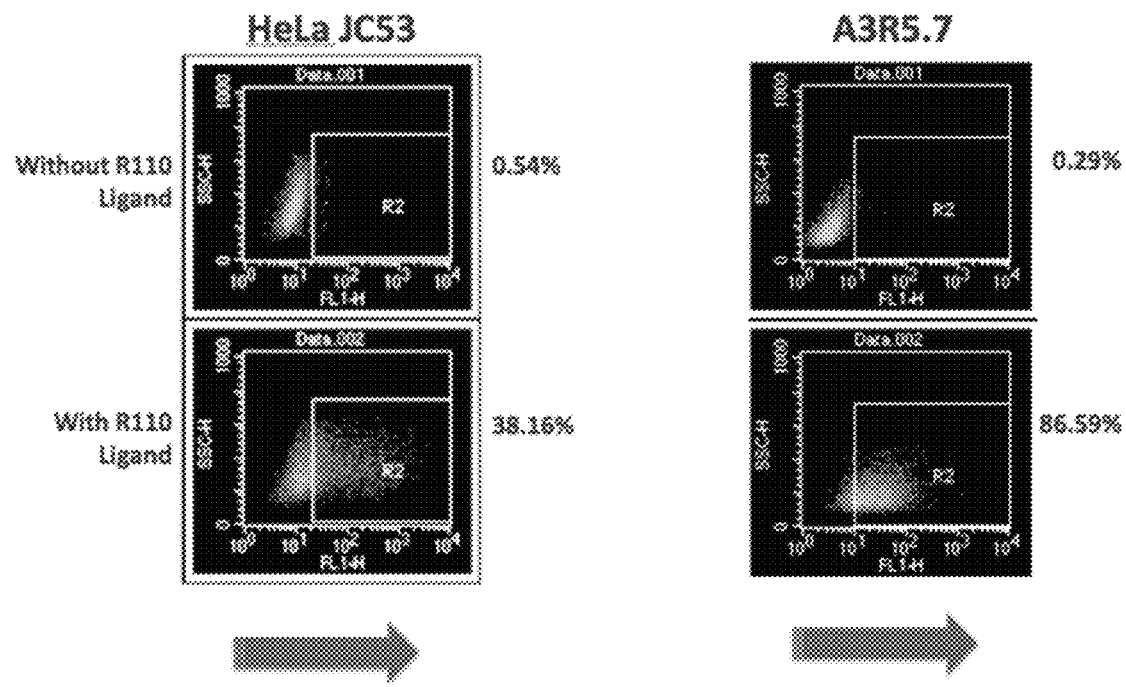
FIGS. 9A-9C show the results of screening HeLa JC53 and A3R5.7 for Halotage expression.
Figure 9B:
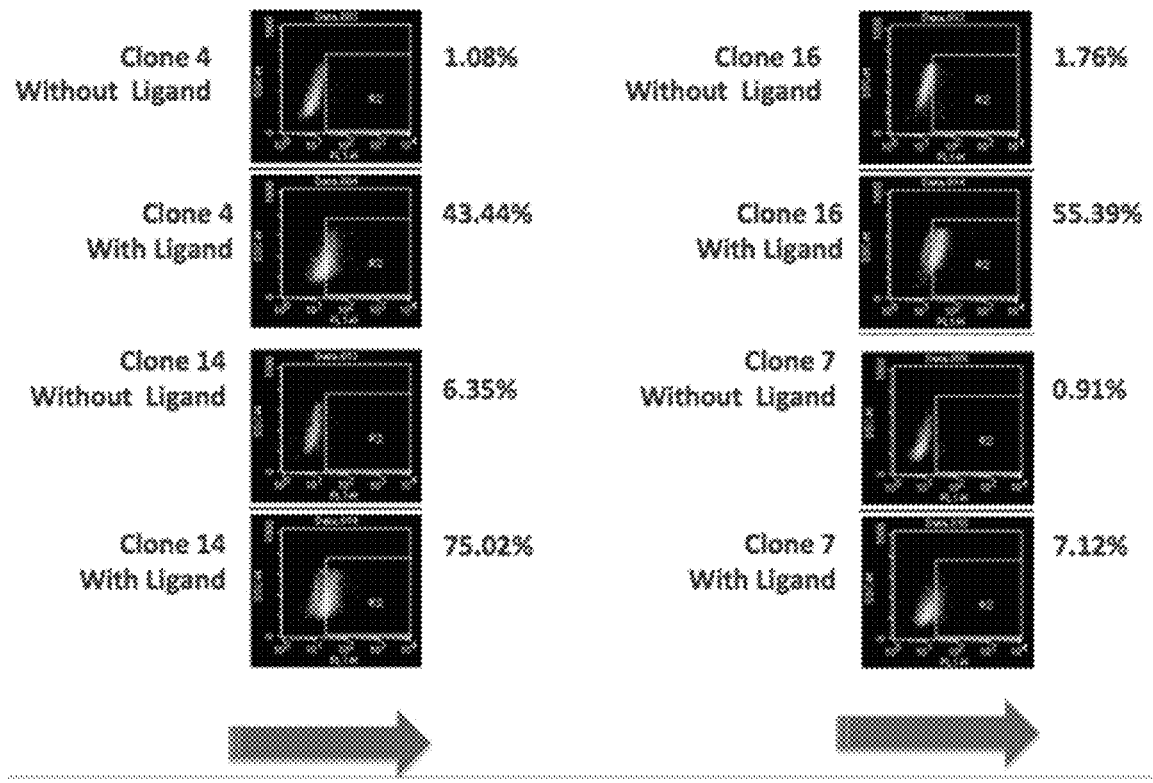
Figure 9C:
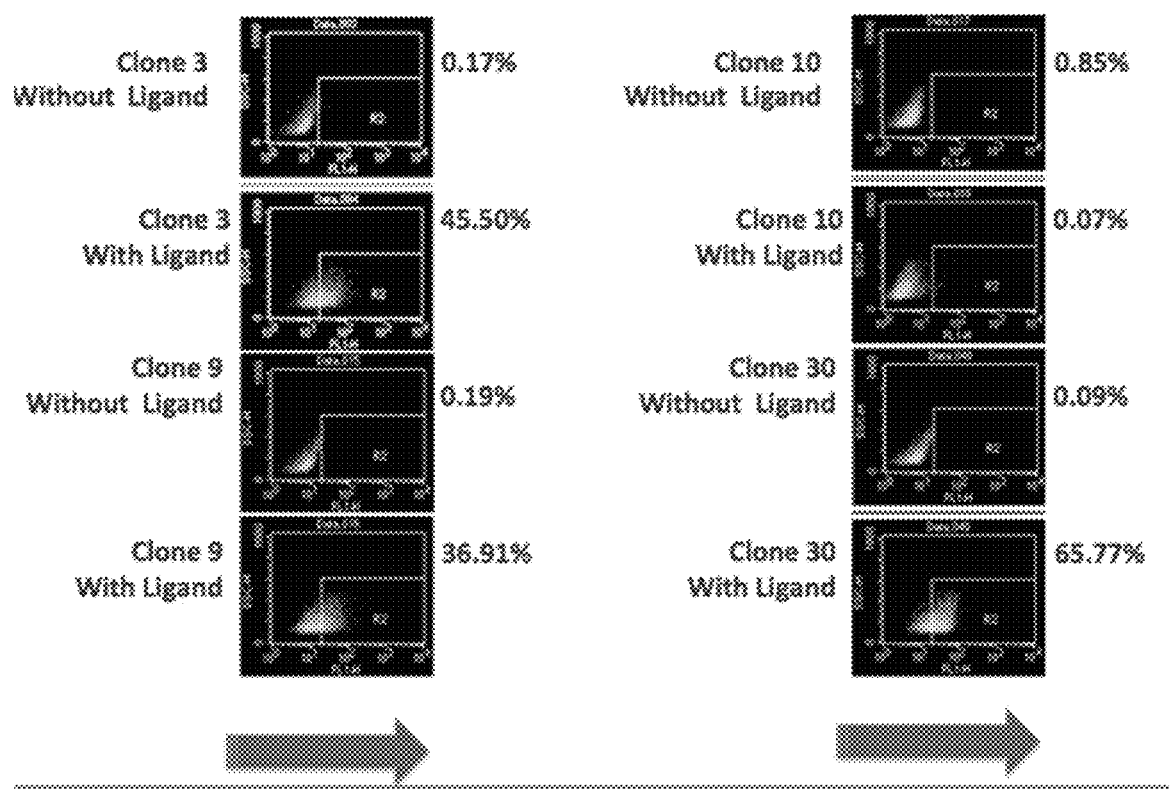
Figure 10A:
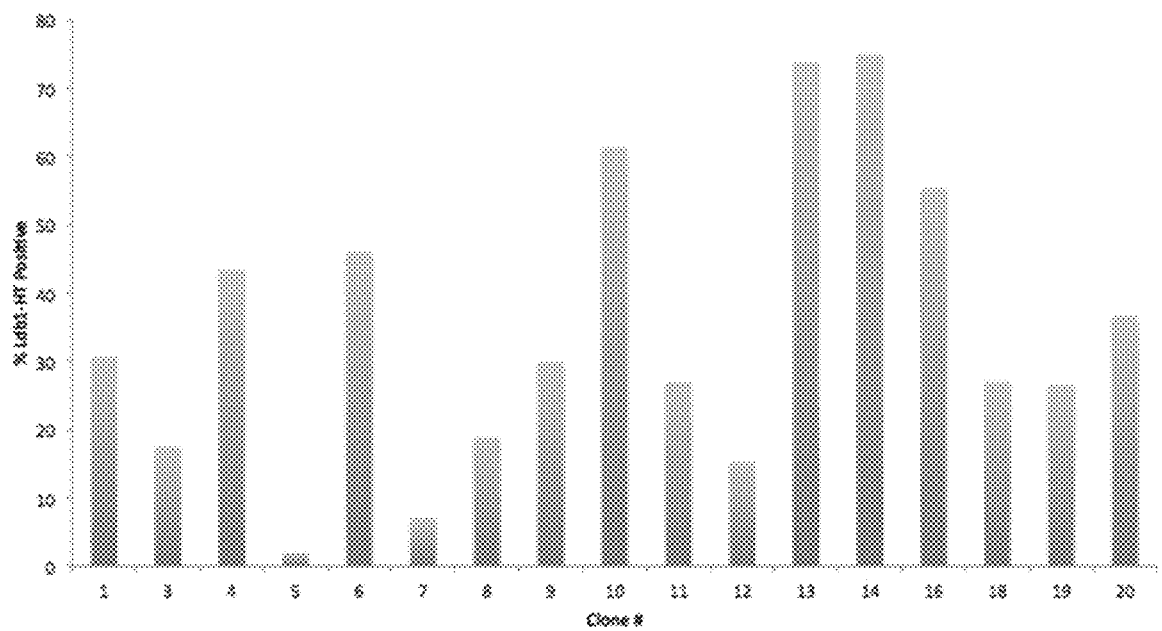
FIGS. 10A-10B show a summary of vLKO.1 MCS Puro Ldb1-HT transduced HeLa JC53 and A3R5.7 clones tested (FACS R110 direct ligand).
Figure 10B:
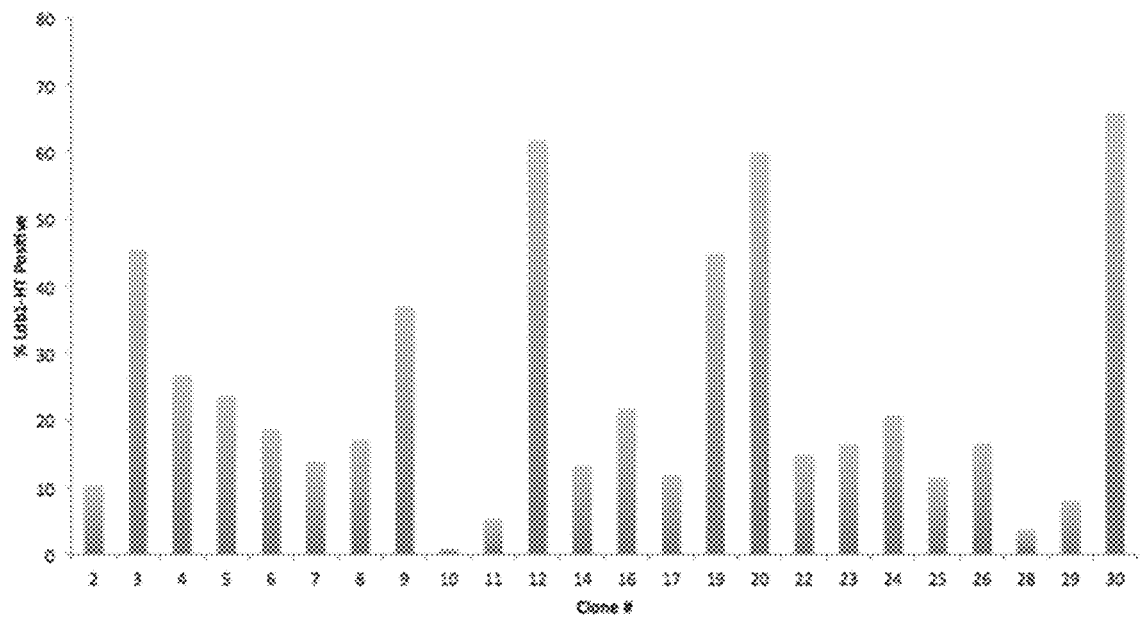

Halotag-Ldb1 Fusion Protein. Ldb1-Halotag was cloned into a modified version of the commercially available pLKO.1 lentiviral vector (MCS cloned into commercial PLKO.1). The proper pLKO.1 MCS Puro Ldb1-HT vector size was confirmed by restriction enzyme digest and agarose gel electrophoresis (FIG. 8). The resulting vector was termed pLKO.1 MCS Puro Ldb1-HT and was packaged using HEK293T cells with the helper plasmid pCMVA8.2 and pCMV-VSV-G. The lentiviral particles, vPLKO.1 MCS Puro Ldb1-HT, were utilized to transduce HeLa JC53 and A3R5.7 cells to constitutively express the Ldb1-HT fusion protein. Puromycin selection was performed to propagate the transduced cells and subsequently screened via FACS for Halotag expression using the Halotag Direct Ligand R110 (Promega). Individual clones were isolated from polyclonal populations of Ldb1-HT transduced cells by limiting dilution. The HeLa JC53 and A3R5.7 clones were also screened for Halotag expression using the Halotag R110 Direct Ligand via FACS (FIGS. 9 and 10).

Figure 11:
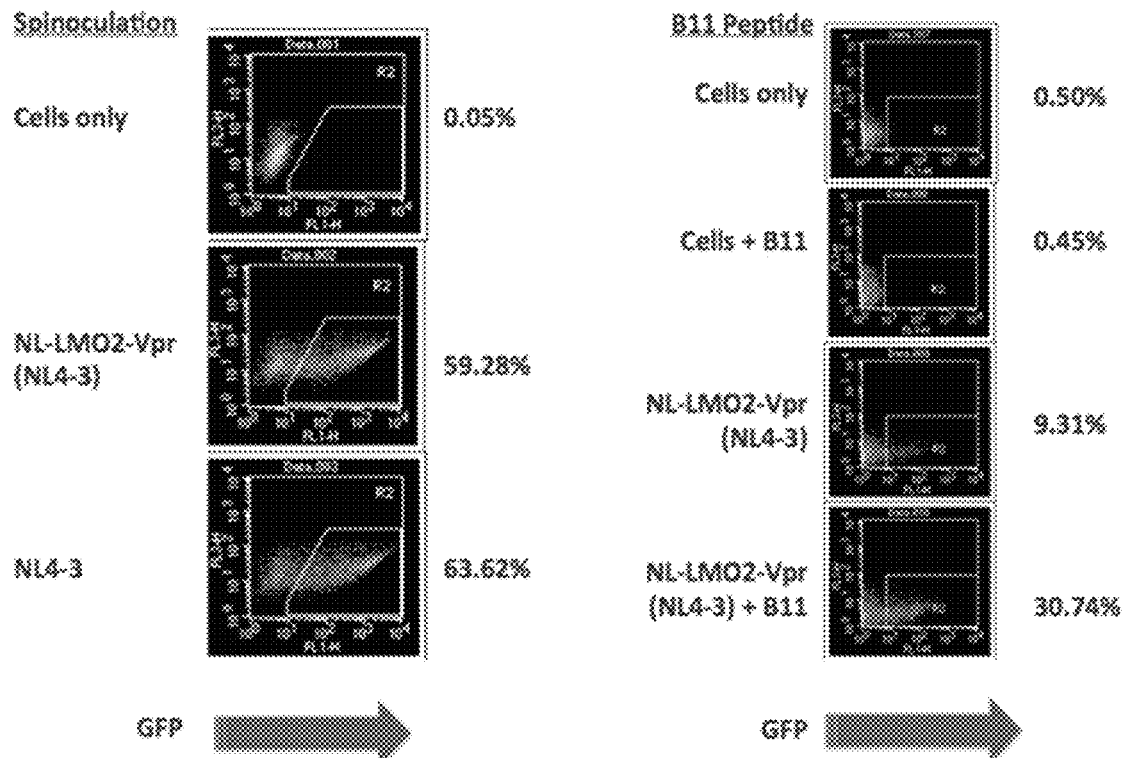
FIG. 11 compares the infectivity of vNL-LMO2-Vpr versus the Clone 8 Rev-dependent GFP reporter cell line.

NL-LMO2-Vpr Fusion Protein. The plasmid pNL-LMO2-Vpr was provided by Promega and was packaged into the NL4-3 virion by co-transfecting pNL-LMO2-Vpr and pNL4-3 into HEK293T cells. The supernatant was harvested after 48 hours, centrifuged at 1200 rpm, decanted to remove cell debris, and 0.45 µM syringe-end filtered. Aliquots of the viral particles, vNL-LMO2-Vpr (NL4-3), were stored frozen at −80° C. The infectivity of the vNL-LMO2-Vpr (NL4-3) was determined using a Rev-dependent GFP reporter cell line (FIG. 11).

HIV-1 Nuclear Migration BRET Assay. An assessment was performed of the BRET signal generated in the assay following the infection of either Ldb1-HT transduced HeLa JC53 or A3R5.7 cells with vNL-LMO2-Vpr (NL4-3) was evaluated.

Figure 12:
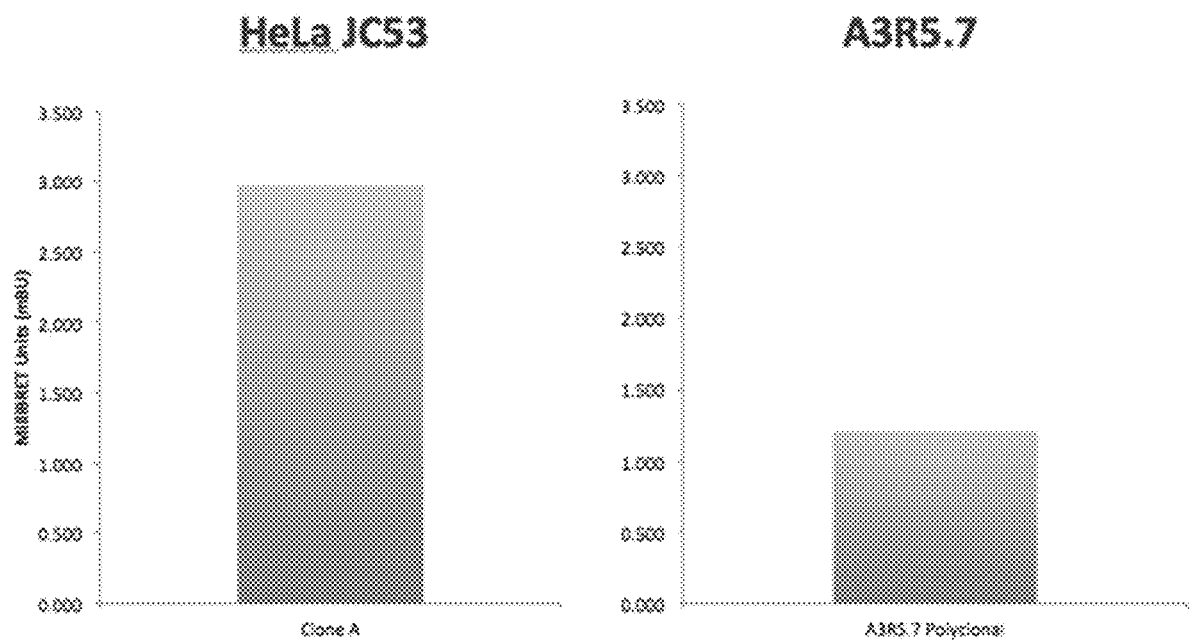
FIG. 12 is a bar graph showing the BRET results of the HeLaJC53 and A3R5.7 Ldb1-HT transduced cells (6-hour infection).
Figure 13:
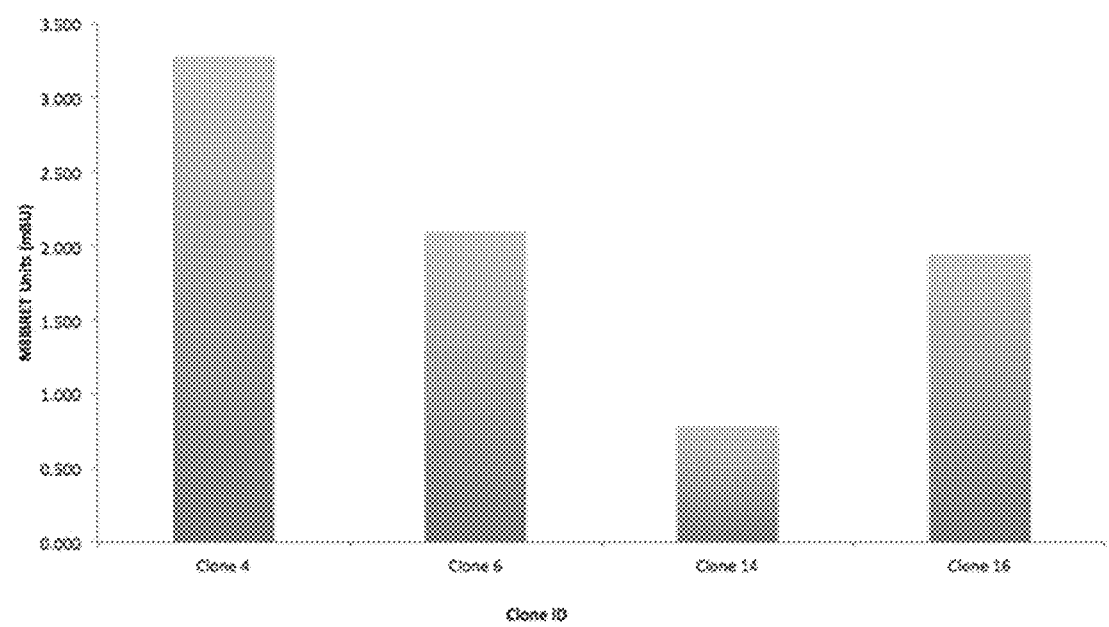
FIG. 13 is a bar graph showing the BRET results of the HeLaJC53 Ldb1-HT transduced cells (6-hour infection).

The adherent HeLa JC53 Ldb1-HT transduced cells with and without the NanoBRET 618 ligand were added to triplicate wells of a sterile white clear bottom 96-well microtiter plate (Greiner 655098) and infected with vNL-LMO2-Vpr (NL4-3) an initial 2-hour period at 37° C. At the conclusion of the 2-hour infection, the cells were washed 2× with PBS and 2004 complete culture medium was added to each well. The plates were incubated for an additional 4-hours at 37° C. (6-hour total infection time) or as otherwise indicated. At the conclusion of this incubation, the plates were washed 2× with PBS and 100 µL of PBS was added to each well. 25 µL of diluted NanoBRET substrate was added to each well and the plates were read on a Promega Glowmax Discover Luminometer using the default BRET Ratio instrument settings (donor signal-emission 450 nm/BP 80 nm; acceptor signal-emission 610 nm/LP). The NanoBRET ratio was calculated for each sample using the following formula: Acceptor Emission (618 nm)/Donor Emission (460 nm)=×1,000=milliBRET units (mBU). To account for donor-contributed background or bleed-through, the without ligand-no-acceptor control samples wee subtracted from the with ligand experimental samples to obtain the corrected NanoBRET ratio. Representative BRET results are included in FIGS. 12 and 13.

Figure 14:
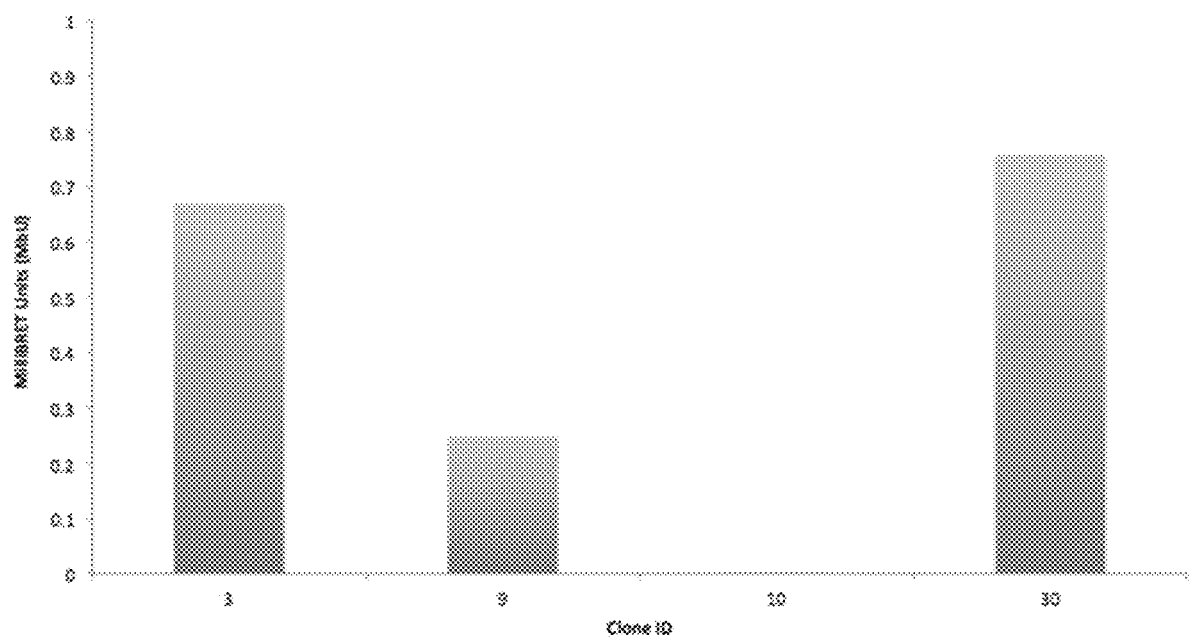
FIG. 14 is a bar graph showing the BRET results of the A3R5.7 Ldb1-HT transduced cells (6-hour infection).

For the suspension of the A3R5.7 Ldb1-HT transduced cells, cells with and without Halotag 618 ligand were incubated overnight at 37° C. in 5 mL polypropylene tubes with caps. At the conclusion of the overnight incubation, the cells were pelleted at 1200 rpm and re-suspended to 200 μL with PBS. The cells were infected with vNL-LMO2-Vpr (NL4-3) an initial 2-hour period at 37° C. At the conclusion of the 2-hour infection, the cells were washed 2× with PBS and re-suspended to 0.5 mL with complete culture medium. The plates were incubated for an additional 4-hours at 37° C. (6-hour total infection time) or as otherwise specified. At the end of the specified incubation time, the cells were washed 2× with PBS and re-suspended to a final volume of 500 μL with PBS. 100μ of the re-suspended cells were added to sterile white clear bottom 96-well microtiter plates (Greiner 655098). 25 μL of diluted NanoBRET substrate was added to each well and the plates were read on a Promega Glowmax Discover Luminometer using the default BRET Ratio instrument settings (donor signal-emission 450 nm/BP 80 nm; acceptor signal-emission 610 nm/LP). The NanoBRET ratio was calculated for each sample using the following formula: Acceptor Emission (618 nm)/Donor Emission (460 nm)=×1,000=milliBRET units (mBU). To account for donor-contributed background or bleed-through, the without ligand-no-acceptor control samples wee subtracted from the with ligand experimental samples to obtain the corrected NanoBRET ratio. Representative BRET results are included in FIGS. 12 and 14.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The present invention comprises the sequences referred to herein, SEQ. ID NOs: 1-7, and the full sequences are provided herein below.

What is claimed is:

1. A recombinant DNA construct comprising a promotor operably linked to a nucleotide sequence encoding a fusion protein comprising a LIM Domain Only Protein 2 (LMO2) polypeptide, a reporter polypeptide, and a Viral Protein R (Vpr), wherein the Vpr polypeptide comprises the polypeptide encoded by SEQ ID NO: 5; and wherein the LMO2 polypeptide comprises the polypeptide encoded by SEQ ID NO: 1.

2. The recombinant DNA construct of claim 1, wherein the LMO2 polypeptide is fused to the N-terminus of the reporter polypeptide.

3. The recombinant DNA construct of claim 1, wherein the LMO2 polypeptide is fused to the C-terminus of the reporter polypeptide.

4. The recombinant DNA construct of claim 1, wherein the LMO2 polypeptide is fused to the N-terminus of the Vpr polypeptide.

5. The recombinant DNA construct of claim 1, wherein the LMO2 polypeptide is fused to the C-terminus of the Vpr polypeptide.

6. The recombinant DNA construct of claim 1, wherein the reporter polypeptide is a luciferase; wherein the fusion protein comprises the reporter polypeptide at the N-terminus of the fusion protein; wherein the C-terminus of the reporter polypeptide is fused to the N-terminus of the Vpr polypeptide; and wherein the fusion protein comprises the Vpr polypeptide at the C-terminus of the fusion protein.

7. The recombinant DNA construct of claim 1, wherein the reporter polypeptide is a luciferase; wherein the fusion protein comprises the reporter polypeptide at the N-terminus of the fusion protein; wherein the C-terminus of the reporter polypeptide is fused to the N-terminus of the Vpr polypeptide; wherein the fusion protein comprises the Vpr at the C-terminus of the fusion protein; wherein the reporter polypeptide comprises the polypeptide encoded by SEQ ID NO: 2.

8. The recombinant DNA construct of claim 1, wherein the reporter polypeptide is a green fluorescent protein; wherein the fusion protein comprises the reporter polypeptide at the N-terminus of the fusion protein; wherein the C-terminus of the reporter polypeptide is fused to the N-terminus of the Vpr polypeptide; wherein the fusion protein comprises the Vpr at the C-terminus of the fusion protein; wherein the reporter polypeptide comprises the polypeptide encoded by SEQ ID NO: 3.

9. The recombinant DNA construct of any one of claims 1-5, wherein the reporter polypeptide is a luciferase.

10. The recombinant DNA construct of claim 9, wherein the luciferase comprises a polypeptide encoded by SEQ ID NO: 2.

11. The recombinant DNA construct of any one of claims wherein the reporter polypeptide is a fluorescent protein.

12. The recombinant DNA construct of claim 11, wherein the fluorescent protein is a green fluorescent protein.

13. The recombinant DNA construct of claim 12, wherein the green fluorescent protein comprises a polypeptide encoded by SEQ ID NO: 3.

14. The recombinant DNA construct of any one of claims wherein the reporter polypeptide is a bacterial dehalogenase capable of binding a fluorescent ligand.

15. The recombinant DNA construct of claim 14, wherein the bacterial dehalogenase comprises a polypeptide sequence encoded by SEQ ID NO: 4.

16. The recombinant DNA construct of claim 14, wherein the fluorescent ligand has a structure represented by the formula

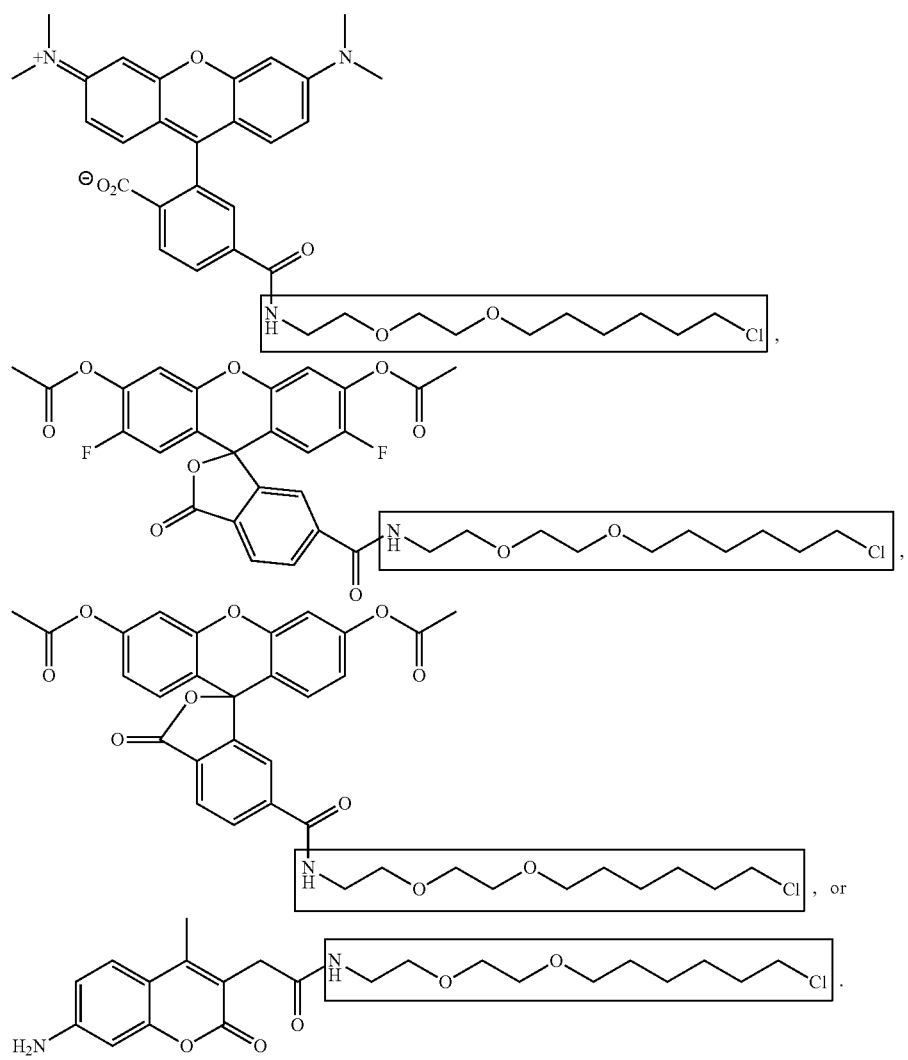

17. A recombinant virus particle comprising the fusion protein encoded by the recombinant DNA construct of any one of claims 1-8.

18. A method of preparing a recombinant virus particle, comprising cotransfection of a cell-line with the recombinant DNA construct of any one of claims 1-8 and at least one proviral plasmid.

19. The method of claim 18, further comprising isolating the virus particles.

20. The method of claim 19, further comprising concentrating the virus particles.

21. The method of claim 18, wherein the virus particles are HIV virus particles.

22. The method of claim 18, wherein the proviral plasmid comprises pNL4-3.

23. The method of claim 18, wherein the virus particles are lentivirus particles.

24. The method of claim 23, wherein the proviral plasmid comprises a packaging plasmid and an envelope plasmid.

* * * * *

SEQUENCE LISTING

```
<160> NUMBER OF SEQ ID NOS: 7

<210> SEQ ID NO 1
<211> LENGTH: 681
<212> TYPE: DNA
<213> ORGANISM: Artificial Sequence
<220> FEATURE:
<223> OTHER INFORMATION: Synthetic construct

<400> SEQUENCE: 1
atggaaggga gcgcggtgac tgtccttgag cgcggagggg cgagctcgcc ggcggagcgc      60
cggagcaagc ggaggcgcag gagcggcggc gacggcggcg gcggcggcgg cgcccgagca     120 cccgagggg tccgagcccc ggcagccggc cagccccgcg ccacaaaggg agcgccccg      180 ccgcccggca ccccgcctcc ctccccaatg tcctcggcca tcgaaaggaa gagcctggac     240
ccttcagagg aaccagtgga tgaggtgctg cagatccccc catccctgct gacatgcggc     300
ggctgccagc agaacattgg ggaccgctac ttcctgaagg ccatcgacca gtactggcac     360
gaggactgcc tgagctgcga cctctgtggc tgccggctgg gtgaggtggg gcggcgcctc     420
tactacaaac tgggccggaa gctctgccgg agagactatc tcaggctttt tgggcaagac     480
ggtctctgcg catcctgtga caagcggatt cgtgcctatg agatgacaat gcgggtgaaa     540
gacaaagtgt atcacctgga atgtttcaaa tgcgccgcct gtcagaagca tttctgtgta     600
ggtgacagat acctcctcat caactctgac atagtgtgcg aacaggacat ctacgagtgg     660
actaagatca atgggatgat a                                               681

<210> SEQ ID NO 2
<211> LENGTH: 516
<212> TYPE: DNA
<213> ORGANISM: Artificial Sequence
<220> FEATURE:
<223> OTHER INFORMATION: Synthetic sequence

<400> SEQUENCE: 2
atggtcttca cactcgaaga tttcgttggg gactggcgac agacagccgg ctacaacctg      60
```

```
gaccaagtcc ttgaacaggg aggtgtgtcc agtttgtttc agaatctcgg ggtgtccgta    120
actccgatcc aaaggattgt cctgagcggt gaaaatgggc tgaagatcga catccatgtc    180
atcatcccgt atgaaggtct gagcggcgac caaatgggcc agatcgaaaa aattttaag    240 gtggtgtacc ctgtggatga tcatcacttt aaggtgatcc tgcactatgg cacactggta    300
atcgacgggg ttacgccgaa catgatcgac tatttcggac ggccgtatga aggcatcgcc    360
gtgttcgacg gcaaaaagat cactgtaaca gggaccctgt ggaacggcaa caaaattatc    420
gacgagcgcc tgatcaaccc cgacggctcc ctgctgttcc gagtaaccat caacggagtg    480
accggctggc ggctgtgcga acgcattctg gcgtaa                              516

<210> SEQ ID NO 3
<211> LENGTH: 717
<212> TYPE: DNA
<213> ORGANISM: Artificial Sequence
<220> FEATURE:
<223> OTHER INFORMATION: Synthetic construct

<400> SEQUENCE: 3
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca cctgacctc cggcgtgcag tgcttcagcc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaag       717

<210> SEQ ID NO 4
<211> LENGTH: 891
<212> TYPE: DNA
<213> ORGANISM: Artificial sequence
<220> FEATURE:
<223> OTHER INFORMATION: Synthetic construct

<400> SEQUENCE: 4
atggcagaaa tcggtactgg ctttccattc gacccccatt atgtggaagt cctgggcgag     60
cgcatgcact acgtcgatgt tggtccgcgc gatggcaccc tgtgctgtt cctgcacggt    120 aacccgacct cctcctacgt gtggcgcaac atcatcccgc atgttgcacc gacccatcgc    180
tgcattgctc cagacctgat cggtatgggc aaatccgaca accagacct gggttatttc    240 ttcgacgacc acgtccgctt catggatgcc ttcatcgaag ccctgggtct ggaagaggtc    300
gtcctggtca ttcacgactg gggctccgct ctgggttttc actgggccaa gcgcaatcca    360
gagcgcgtca aggtattgc atttatggag ttcatccgcc ctatcccgac ctgggacgaa    420
tggccagaat ttgcccgcga gaccttccag gccttccgca ccaccgacgt cggccgcaag    480
ctgatcatcg atcagaacgt ttttatcgag ggtacgctgc cgatgggtgt cgtccgcccg    540
```

```
ctgactgaag tcgagatgga ccattaccgc gagccgttcc tgaatcctgt tgaccgcgag    600
ccactgtggc gcttcccaaa cgagctgcca atcgccggtg agccagcgaa catcgtcgcg    660
ctggtcgaag aatacatgga ctggctgcac cagtcccctg tcccgaagct gctgttctgg    720
ggcaccccag gcgttctgat cccaccggcc gaagccgctc gcctggccaa agcctgcct    780 aactgcaagg ctgtggacat cggcccgggt ctgaatctgc tgcaagaaga caacccggac    840
ctgatcggca gcgagatcgc gcgctggctg tcgacgctcg agatttccgg c             891

<210> SEQ ID NO 5
<211> LENGTH: 291
<212> TYPE: DNA
<213> ORGANISM: Artificial Sequence
<220> FEATURE:
<223> OTHER INFORMATION: Synthetic construct

<400> SEQUENCE: 5
atggaacaag ccccagaaga ccagggaccg cagagggaac catacaatga atggacacta     60
gaacttttag aggaactcaa gcgggaagca gtcagacact ttcctagacc atggcttcat    120
ggcttaggac aacatatcta tgaaacctat ggagatactt ggacgggggt ggaagctata    180
ataagaattc tgcaacgact actgtttgtc catttcagaa ttgggtgcca gcatagccga    240
ataggcattc taagacagag aagagcaaga atggagccag tagatcctaa                291

<210> SEQ ID NO 6
<211> LENGTH: 1128
<212> TYPE: DNA
<213> ORGANISM: Artificial Sequence
<220> FEATURE:
<223> OTHER INFORMATION: Synthetic construct

<400> SEQUENCE: 6
atgctggata gggatgtggg cccaactccc atgtatccgc ctacatacct ggagccaggg     60
attgggaggc acaccata tggcaaccaa actgactaca gaatatttga gcttaacaaa     120
cggcttcaga actggacaga ggagtgtgac aatctctggt gggatgcatt cacgactgag    180
ttctttgagg atgatgccat gttgaccatc actttctgcc tggaggatgg accaaagaga    240
tataccattg gccggaccct gatcccacgc tacttccgca gcatctttga ggggggtgct    300
acggagctgt actatgttct taagcacccc aaggaggcat tccacagcaa ctttgtgtcc    360
ctcgactgtg accagggcag catggtgacc cagcatggca gcccatgtt cacccaggtg    420 tgtgtggagg gccggttgta cctggagttc atgtttgacg acatgatgcg ataaagacg    480 tggcacttca gcatccggca gcaccgagag ctcatccccc gcagcatcct tgccatgcat    540
gcccaagacc cccagatgtt ggatcagctc tccaaaaaca tcactcggtg tgggctgtcc    600
aattccactc tcaactacct ccgactctgt gtgatactcg agcccatgca agagctcatg    660
tcacgccaca agacctacag cctcagcccc cgcgactgcc tcaagacctg ccttttccag    720
aagtggcagc gcatggtagc acccctgcg gagcccacac gtcagcagcc cagcaaacgg    780
cggaaacgga agatgtcagg gggcagcacc atgagctctg tggtggcaa caccaacaac    840 agcaacagca agaagaagag cccagctagc accttcgccc tctccagcca ggtacctgat    900
gtgatggtgg tggggggagcc caccctgatg gcgggggagt tcggggacga ggacgagagg    960
ctcatcaccc ggctggagaa cacccagttt gacgcagcca acggcattga cgacgaggac   1020 agcttaaca actcccctgc actgggcgcc aacagcccct ggaacagcaa gcctccgtcc   1080
agccaagaaa gcaaatcgga gaaccccacg tcacaggcct cccagtaa              1128
```

```
<210> SEQ ID NO 7
<211> LENGTH: 711
<212> TYPE: DNA
<213> ORGANISM: Artificial Sequence
<220> FEATURE:
<223> OTHER INFORMATION: Synthetic construct

<400> SEQUENCE: 7
atggtgagca agggcgagga ggataacatg gccatcatca aggagttcat gcgcttcaag      60
gtgcacatgg agggctccgt gaacggccac gagttcgaga tcgagggcga gggcgagggc     120
cgcccctacg agggcaccca gaccgccaag ctgaaggtga ccaagggtgg ccccctgccc     180
ttcgcctggg acatcctgtc ccctcagttc atgtacggct ccaaggccta cgtgaagcac     240
cccgccgaca tccccgacta cttgaagctg tccttccccg agggcttcaa gtgggagcgc     300
gtgatgaact tcgaggacgg cggcgtggtg accgtgaccc aggactcctc cctgcaggac     360
ggcgagttca tctacaaggt gaagctgcgc ggcaccaact tccctccga cggcccgta     420 atgcagaaga agaccatggg ctgggaggcc tcctccgagc ggatgtaccc cgaggacggc     480
gccctgaagg gcgagatcaa gcagaggctg aagctgaagg acggcggcca ctacgacgct     540
gaggtcaaga ccacctacaa ggccaagaag cccgtgcagc tgcccggcgc ctacaacgtc     600
aacatcaagt tggacatcac ctcccacaac gaggactaca ccatcgtgga acagtacgaa     660
cgcgccgagg gccgccactc caccggcggc atggacgagc tgtacaagta a             711
```